United States Patent
Bao

(10) Patent No.: US 11,680,029 B2
(45) Date of Patent: Jun. 20, 2023

(54) PROCESSES FOR UPGRADING ALKANES AND ALKYL AROMATIC HYDROCARBONS

(71) Applicant: ExxonMobil Chemical Patents Inc., Baytown, TX (US)

(72) Inventor: Xiaoying Bao, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 17/166,082

(22) Filed: Feb. 3, 2021

(65) Prior Publication Data

US 2021/0276932 A1 Sep. 9, 2021

Related U.S. Application Data

(60) Provisional application No. 62/986,229, filed on Mar. 6, 2020.

(30) Foreign Application Priority Data

Jun. 11, 2020 (EP) ..................... 20179508

(51) Int. Cl.
*C07C 5/333* (2006.01)
*B01J 23/96* (2006.01)
(Continued)

(52) U.S. Cl.
CPC ............. *C07C 5/3337* (2013.01); *B01J 23/96* (2013.01); *B01J 38/10* (2013.01); *B01J 38/12* (2013.01); *C07C 11/06* (2013.01); *C07C 2523/42* (2013.01)

(58) Field of Classification Search
None
See application file for complete search history.

(56) References Cited

U.S. PATENT DOCUMENTS 5,633,421 A 5/1997 Iezzi et al.
5,922,925 A 7/1999 Akporiaye et al.
(Continued)

FOREIGN PATENT DOCUMENTS

WO 1997/041192 11/1997
WO WO-2018193668 A1 * 10/2018 ............ B01J 37/088
WO 2020/046978 3/2020

OTHER PUBLICATIONS

ChemIDplus "Hydrotalcite" https://chem.nlm.nih.gov/chemidplus/rn/12304-65-3. Retrieved May 3, 2022. (Year: 2022).*
(Continued)

*Primary Examiner* — In Suk C Bullock
*Assistant Examiner* — Alyssa L Cepluch

(57) ABSTRACT

Processes for upgrading a hydrocarbon. The process can include (I) contacting a hydrocarbon-containing feed with a catalyst that can include a Group 8-10 element or a compound thereof disposed on a support to effect one or more of dehydrogenation, dehydroaromatization, and dehydrocyclization of at least a portion of the hydrocarbon-containing feed to produce a coked catalyst and an effluent. The process can also include (II) contacting at least a portion of the coked catalyst with an oxidant to effect combustion of at least a portion of the coke to produce a regenerated catalyst. The process can also include (III) contacting an additional quantity of the hydrocarbon-containing feed with at least a portion of the regenerated catalyst. A cycle time from the contacting the hydrocarbon-containing feed with the catalyst in step (I) to the contacting the additional hydrocarbon-containing feed with the regenerated catalyst in step (III) can be ≤5 hours.

22 Claims, 1 Drawing Sheet

(51) Int. Cl.
*B01J 38/10* (2006.01)
*B01J 38/12* (2006.01)
C07C 11/06 (2006.01)

(56) References Cited

U.S. PATENT DOCUMENTS

| | | |
|---|---|---|
| 6,746,597 B2 | 6/2004 | Zhou et al. |
| 8,546,286 B2 | 10/2013 | McCarthy et al. |
| 8,653,317 B2 * | 2/2014 | Pierce .................. C07C 5/3337 585/440 |
| 9,511,356 B2 | 12/2016 | Vaidya et al. |
| 2002/0098976 A1 * | 7/2002 | Rytter .................. C07C 5/3337 502/340 |
| 2010/0236985 A1 | 9/2010 | Luo et al. |
| 2017/0151553 A1 * | 6/2017 | Lee ......................... B01J 23/63 |
| 2018/0029015 A1 * | 2/2018 | Mondal ................. B01J 35/002 |
| 2020/0038852 A1 | 2/2020 | Kimura et al. |
| 2020/0055028 A1 | 2/2020 | Choi et al. |

OTHER PUBLICATIONS

"Sintering and redispersion behavior of Pt on Pt/MgO" (Journal of Catalysis, vol. 257, Issue 1, Jul. 1, 2008, pp. 117-124) Tanabe et al.
"Studies on Redispersion and Stability of Platinum in Pt/MgO System during Oxygen Treatment at High Temperatures" (Z. anorg. allg. Chem. 542 (1986) 232-240) Szymura.
"Catalytic Dehydrogenation of Light Alkanes on Metals and Metal Oxides" (Chem. Rev. 2014, 114, 10613-10653) Sattler et al.

* cited by examiner

PROCESSES FOR UPGRADING ALKANES AND ALKYL AROMATIC HYDROCARBONS

CROSS-REFERENCE OF RELATED APPLICATIONS

This application claims priority to and the benefit of U.S. Provisional Application No. 62/986,229, filed Mar. 6, 2020 and EP Application No. 20179508.5, filed Jun. 11, 2020, the disclosures of both of which are incorporated herein by reference in their entirety.

FIELD

This disclosure relates to processes for upgrading alkanes and/or alkyl aromatic hydrocarbons. More particularly, this disclosure relates to processes for dehydrogenating, dehydroaromatizing, and/or dehydrocyclizing one or more alkane and/or one or more alkyl aromatic hydrocarbons in the presence of a catalyst to produce an effluent that includes one or more upgraded hydrocarbons.

BACKGROUND

Catalytic dehydrogenation, dehydroaromatization, and dehydrocyclization of alkane and/or alkyl aromatic hydrocarbons are industrially important chemical conversion processes that are endothermic and equilibrium-limited. The dehydrogenation of alkanes, e.g., $C_2$-$C_{12}$ alkanes, and/or alkyl aromatics, e.g., ethylbenzene, can be done through a variety of different supported catalyst systems such as the Pt-based, Cr-based, Ga-based, V-based, Zr-based, In-based, W-based, Mo-based, Zn-based, and Fe-based systems. Among the existing propane dehydrogenation processes, certain process uses an alumina supported chromia catalyst that provides one of the highest propylene yields of approximately 50% (55% propane conversion at 90% propylene selectivity)), which is obtained at a temperature of approximately 560° C. to 650° C. and at a low pressure of 20 kPa-absolute to 50 kPa-absolute. It is desirable to increase the propylene yield without having to operate at such low pressure to increase the efficiency of the dehydrogenation process.

Increasing the temperature of the dehydrogenation process is one way to increase the conversion of the process according to the thermodynamics of the process. For example, at 670° C., 100 kPa-absolute, in the absence of any inert/diluent, the equilibrium yield propylene yield has been estimated via simulation to be approximately 74%. At such high temperature, however, the catalyst deactivates very rapidly and/or the propylene selectivity becomes uneconomically low. The rapid catalyst deactivation is believed to be caused by coke depositing onto the catalyst and/or agglomeration of the active phase. Coke can be removed by combustion using an oxygen-containing gas, however, agglomeration of the active phase is believed to be exacerbated during the combustion process, which rapidly reduces the activity and stability of the catalyst.

There is a need, therefore, for improved processes and catalysts for dehydrogenating, dehydroaromatizing, and/or dehydrocyclizing alkane and/or alkyl aromatic hydrocarbons. This disclosure satisfies this and other needs.

SUMMARY

Processes for upgrading alkanes and/or alkyl aromatic hydrocarbons are provided. In some embodiments, the process for upgrading a hydrocarbon can include (I) contacting a hydrocarbon-containing feed with a catalyst that can include Pt disposed on a support to effect one or more of dehydrogenation, dehydroaromatization, and dehydrocyclization of at least a portion of the hydrocarbon-containing feed to produce a coked catalyst and an effluent that can include one or more upgraded hydrocarbons and molecular hydrogen. The hydrocarbon-containing feed can include one or more of $C_2$-$C_{16}$ linear or branched alkanes, or one or more of $C_4$-$C_{16}$ cyclic alkanes, or one or more $C_8$-$C_{16}$ alkyl aromatics, or a mixture thereof. The hydrocarbon-containing feed and catalyst can be contacted at a temperature in a range from 300° C. to 900° C., for a time period of ≤3 hours, under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatics in the hydrocarbon-containing feed. The catalyst can include from 0.05 wt % to 6 wt % of Pt based on the weight of the support. The one or more upgraded hydrocarbons can include at least one of a dehydrogenated hydrocarbon, a dehydroaromatized hydrocarbon, and a dehydrocyclized hydrocarbon. The process can also include (II) contacting at least a portion of the coked catalyst with an oxidant to effect combustion of at least a portion of the coke to produce a regenerated catalyst lean in coke and a combustion gas. The process can also include (III) contacting an additional quantity of the hydrocarbon-containing feed with at least a portion of the regenerated catalyst to produce a re-coked catalyst and additional effluent. A cycle time from the contacting the hydrocarbon-containing feed with the catalyst in step (I) to the contacting the additional quantity of the hydrocarbon-containing feed with the regenerated catalyst in step (III) can be ≤5 hours.

In other embodiments, the process for upgrading a hydrocarbon can include (I) contacting a hydrocarbon-containing feed with a catalyst that can include a Group 8-10 element disposed on a support to effect one or more of dehydrogenation, dehydroaromatization, and dehydrocyclization of at least a portion of the hydrocarbon-containing feed to produce a coked catalyst and an effluent that can include one or more upgraded hydrocarbons and molecular hydrogen. The hydrocarbon-containing feed can include one or more of $C_2$-$C_{16}$ linear or branched alkanes, or one or more of $C_4$-$C_{16}$ cyclic alkanes, or one or more of $C_8$-$C_{16}$ alkyl aromatics, or a mixture thereof. The hydrocarbon-containing feed and catalyst can be contacted at a temperature in a range from 300° C. to 900° C., for a time period of ≤3 hours, under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatics in the hydrocarbon-containing feed. The one or more upgraded hydrocarbons can include a dehydrogenated hydrocarbon, a dehydroaromatized hydrocarbon, a dehydrocylized hydrocarbon, or a mixture thereof. The catalyst can include from 0.05 wt % to 6 wt % of the Group 8-10 element based on the weight of the support. The support can include at least one of: w wt % of a Group 2 element, x wt % of a Group 4 element, y wt % of a Group 12 element, and z wt % of an element having an atomic number of 21, 39, or 57-71 based on the weight of the support, where w, x, y, and z are independently in a range from 0 to 100, where any Group 2 element is associated with a wt % m based on the weight of the support, any Group 4 element is associated with a wt % n based on the weight of the support, any group 12 element is associated with a wt % p based on the weight of the support, and any element having an atomic number of 21, 39, or 57-71 is associated with a wt % q based on the weight of the support, and m, n, p, and q are independently a number that is in a range from 1 to 100. A sum of w/m+x/n+y/p+z/p can be ≥1, based on the weight of the support. The process can also include (II) contacting at least a portion of the coked catalyst with an oxidant to effect combustion of at least a portion of the coke to produce a regenerated catalyst lean in coke and a combustion gas. The process can also include (III) contacting an additional quantity of the hydrocarbon-containing feed with at least a portion of the regenerated catalyst to produce a re-coked catalyst and additional effluent. A cycle time from the contacting the hydrocarbon-containing feed with the catalyst in step (I) to the contacting the additional quantity of the hydrocarbon-containing feed with the regenerated catalyst in step (III) can be ≤5 hours.

In other embodiments, the process for upgrading a hydrocarbon can include (I) contacting a hydrocarbon-containing feed with a catalyst that can include a Group 8-10 element or a compound thereof disposed on a support to effect one or more of dehydrogenation, dehydroaromatization, and dehydrocyclization of at least a portion of the hydrocarbon-containing feed to produce a coked catalyst and an effluent comprising one or more upgraded hydrocarbons and molecular hydrogen. The hydrocarbon-containing feed can include one or more of $C_2$-$C_{16}$ linear or branched alkanes, or one or more of $C_4$-$C_{16}$ cyclic alkanes, or one or more of $C_8$-$C_{16}$ alkyl aromatics, or a mixture thereof and 0.1 vol % to 50 vol % of steam, based on a total volume of any $C_2$-$C_{16}$ alkanes and any $C_8$-$C_{16}$ alkyl aromatics in the hydrocarbon-containing feed. The hydrocarbon-containing feed and catalyst can be contacted at a temperature in a range from 300° C. to 900° C., for a time period of ≤3 hours, under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatics in the hydrocarbon-containing feed. The catalyst can include from 0.05 wt % to 6 wt % of the Group 8-10 element or a compound thereof based on the weight of the support. The upgraded hydrocarbon can include a dehydrogenated hydrocarbon, a dehydroaromatized hydrocarbon, a dehydrocylized hydrocarbon, or a mixture thereof. The process can also include (II) contacting at least a portion of the coked catalyst with an oxidant to effect combustion of at least a portion of the coke to produce a regenerated catalyst lean in coke and a combustion gas. The process can also include (III) contacting an additional quantity of the hydrocarbon-containing feed with at least a portion of the regenerated catalyst to produce a re-coked catalyst and additional effluent. A cycle time from the contacting the hydrocarbon-containing feed with the catalyst in step (I) to the contacting the additional quantity of the hydrocarbon-containing feed with the regenerated catalyst in step (III) can be ≤5 hours.

DETAILED DESCRIPTION

Figure 1:
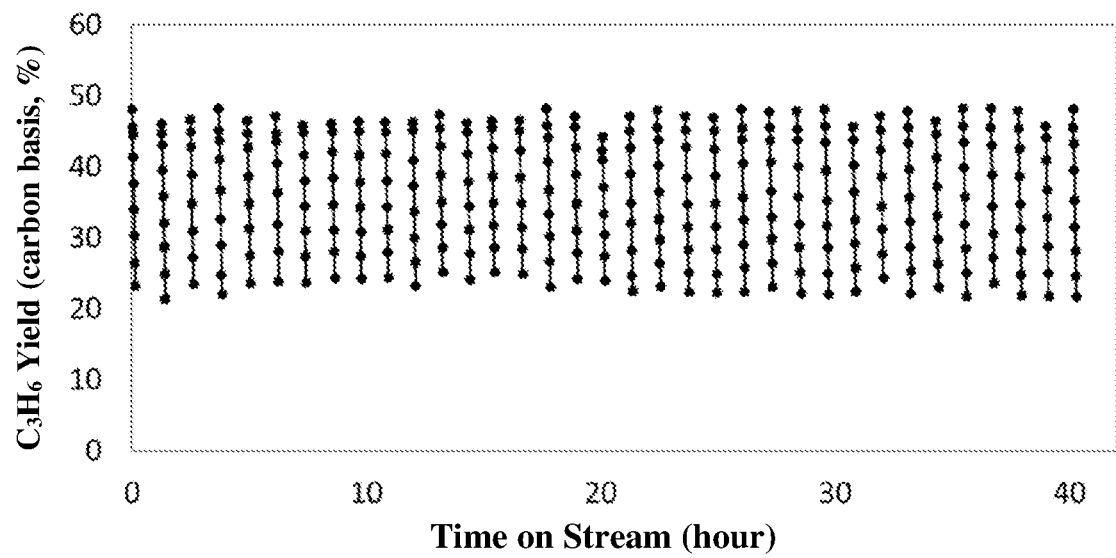
FIG. 1 shows the catalyst stability results of a catalyst used in Examples 1-3 after having undergone 35 cycles (regeneration, reduction, and dehydrogenation) carried out under the same conditions used in Example 1.

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other steps, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and/or equipment used for acquiring the measurement.

Certain embodiments and features are described herein using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated.

The indefinite article "a" or "an", as used herein, means "at least one" unless specified to the contrary or the context clearly indicates otherwise. Thus, embodiments using "a reactor" or "a conversion zone" include embodiments where one, two or more reactors or conversion zones are used, unless specified to the contrary or the context clearly indicates that only one reactor or conversion zone is used.

The term "hydrocarbon" means (i) any compound consisting of hydrogen and carbon atoms or (ii) any mixture of two or more such compounds in (i). The term "Cn hydrocarbon," where n is a positive integer, means (i) any hydrocarbon compound comprising carbon atom(s) in its molecule at the total number of n, or (ii) any mixture of two or more such hydrocarbon compounds in (i). Thus, a C2 hydrocarbon can be ethane, ethylene, acetylene, or mixtures of at least two of these compounds at any proportion. A "Cm to Cn hydrocarbon" or "Cm-Cn hydrocarbon," where m and n are positive integers and m<n, means any of Cm, Cm+1, Cm+2, . . . , Cn−1, Cn hydrocarbons, or any mixtures of two or more thereof. Thus, a "C2 to C3 hydrocarbon" or "C2-C3 hydrocarbon" can be any of ethane, ethylene, acetylene, propane, propene, propyne, propadiene, cyclopropane, and any mixtures of two or more thereof at any proportion between and among the components. A "saturated C2-C3 hydrocarbon" can be ethane, propane, cyclopropane, or any mixture thereof of two or more thereof at any proportion. A "Cn+ hydrocarbon" means (i) any hydrocarbon compound comprising carbon atom(s) in its molecule at the total number of at least n, or (ii) any mixture of two or more such hydrocarbon compounds in (i). A "Cn– hydrocarbon" means (i) any hydrocarbon compound comprising carbon atoms in its molecule at the total number of at most n, or (ii) any mixture of two or more such hydrocarbon compounds in (i). A "Cm hydrocarbon stream" means a hydrocarbon stream consisting essentially of Cm hydrocarbon(s). A "Cm-Cn hydrocarbon stream" means a hydrocarbon stream consisting essentially of Cm-Cn hydrocarbon(s).

For the purposes of this disclosure, the nomenclature of elements is pursuant to the version of the Periodic Table of Elements (under the new notation) as provided in Hawley's Condensed Chemical Dictionary, $16^{th}$ Ed., John Wiley & Sons, Inc., (2016), Appendix V. For example, a Group 8 element includes Fe, a Group 9 element includes Co, and a group 10 element includes Ni. The term "metalloid", as used herein, refers to the following elements: B, Si, Ge, As, Sb, Te, and At. In this disclosure, when a given element is indicated as present, it can be present in the elemental state or as any chemical compound thereof, unless it is specified otherwise or clearly indicated otherwise by the context.

The term "alkane" means a saturated hydrocarbon. The term "cyclic alkane" means a saturated hydrocarbon comprising a cyclic carbon ring in the molecular structure thereof. An alkane can be linear, branched, or cyclic.

The term "aromatic" is to be understood in accordance with its art-recognized scope, which includes alkyl substituted and unsubstituted mono- and polynuclear compounds.

The term "rich" when used in phrases such as "X-rich" or "rich in X" means, with respect to an outgoing stream obtained from a device, e.g., a conversion zone, that the stream comprises material X at a concentration higher than in the feed material fed to the same device from which the stream is derived. The term "lean" when used in phrases such as "X-lean" or "lean in X" means, with respect to an outgoing stream obtained from a device, e.g., a conversion zone, that the stream comprises material X at a concentration lower than in the feed material fed to the same device from which the stream is derived.

The term "selectivity" refers to the production (on a carbon mole basis) of a specified compound in a catalytic reaction. As an example, the phrase "an alkane hydrocarbon conversion reaction has a 100% selectivity for an olefin hydrocarbon" means that 100% of the alkane hydrocarbon (carbon mole basis) that is converted in the reaction is converted to the olefin hydrocarbon. When used in connection with a specified reactant, the term "conversion" means the amount of the reactant consumed in the reaction. For example, when the specified reactant is propane, 100% conversion means 100% of the propane is consumed in the reaction. Yield (carbon mole basis) is conversion times selectivity.

Overview

The hydrocarbon-containing feed can be or can include, but is not limited to, one or more alkane hydrocarbons, e.g., $C_2$-$C_{16}$ linear or branched alkanes and/or $C_4$-$C_{16}$ cyclic alkanes, and/or one or more alkyl aromatic hydrocarbons, e.g., $C_8$-$C_{16}$ alkyl aromatics. In some embodiments, the hydrocarbon-containing feed can optionally include 0.1 vol % to 50 vol % of steam, based on a total volume of any $C_2$-$C_{16}$ alkanes and any $C_8$-$C_{16}$ alkyl aromatics in the hydrocarbon-containing feed. In other embodiments, the hydrocarbon-containing feed can include <0.1 vol % of steam or can be free of steam, based on the total volume of any $C_2$-$C_{16}$ alkanes and any $C_8$-$C_{16}$ alkyl aromatics in the hydrocarbon-containing feed. The hydrocarbon-containing feed can be contacted with a catalyst that includes a Group 8-10 element, e.g., Pt, disposed on a support to effect one or more of dehydrogenation, dehydroaromatization, and dehydrocyclization of at least a portion of the hydrocarbon-containing feed to produce a coked catalyst and an effluent that can include one or more upgraded hydrocarbons and molecular hydrogen. The one or more upgraded hydrocarbons can be or can include one or more dehydrogenated hydrocarbons, one or more dehydroaromatized hydrocarbons, one or more dehydrocylized hydrocarbons, or a mixture thereof. The hydrocarbon-containing feed and catalyst can be contacted at a temperature in a range from 300° C. to 900° C. for a first time period of ≤3 hours, under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatics in the hydrocarbon-containing feed. The catalyst can include from 0.05 wt % to 6 wt % of the Group 8-10 element, e.g., Pt, based on the weight of the support. The support can be or can include, but is not limited to, a Group 2 element, a Group 4 element, a Group 12 element, an element having an atomic number of 21, 39, or 57-71, or a compound thereof.

At least a portion of the coked catalyst can be contacted with one or more oxidants to effect combustion of at least a portion of the coke to produce a regenerated catalyst lean in coke and a combustion gas. In some embodiments the process can optionally include contacting at least a portion of the regenerated catalyst with a reducing gas to produce a regenerated and reduced catalyst. An additional quantity of the hydrocarbon-containing feed can be contacted with at least a portion of the regenerated catalyst and/or at least a portion of any regenerated and reduced catalyst to produce a re-coked catalyst and additional effluent. A cycle time from contacting the hydrocarbon-containing feed with the catalyst to contacting the additional quantity of the hydrocarbon-containing feed with the regenerated catalyst can be ≤5 hours.

It has been surprisingly and unexpectedly discovered that the catalyst that includes a Group 8-10 element, e.g., Pt, disposed on the support can remain sufficiently active and stable after many cycles, e.g., at least 15, at least 20, at least 30, at least 40, at least 50, at least 60, at least 70, at least 100 cycles, at least 125 cycles, at least 150 cycles, at least 175 cycles, or at least 200 cycles with each cycle time lasting for ≤5 hours, ≤4 hours, ≤3 hours, ≤2 hours, ≤1 hour, ≤50 minutes, ≤45 minutes, ≤30 minutes, ≤15 minutes, ≤10 minutes, ≤5 minutes, ≤1 minute, ≤30 seconds, or ≤10 seconds. In some embodiments, the cycle time can be from 5 seconds, 30 seconds, 1 minute or 5 minutes to 10 minutes, 20 minutes, 30 minutes, 45 minutes, 50 minutes, 70 minutes, 2 hours, 3 ours, 4 hours, or 5 hours. In some embodiments, after the catalyst performance stabilizes (sometimes the few first cycle can have a relatively poor or relatively good performance, but the performance can eventually stabilize), the process can produce a first upgraded hydrocarbon product yield, e.g., propylene when the hydrocarbon-containing feed includes propane, at an upgraded hydrocarbon selectivity, e.g., propylene, of ≥75%, ≥80%, ≥85%, or ≥90%, or >95% when initially contacted with the hydrocarbon-containing feed, and can have a second upgraded hydrocarbon product yield upon completion of the last cycle (at least 15 cycles total) that can be at least 90%, at least 93%, at least 95%, at least 97%, at least 98%, at least 99%, at least 99.5%, or at least 100% of the first upgraded hydrocarbon product yield at an upgraded hydrocarbon selectivity, e.g., propylene, of ≥75%, ≥80%, ≥85%, or ≥90%, or >95%. Prior to this discovery, it was believed that catalysts having a Group 8-10 element, e.g., Pt, as the active component would not maintain sufficient activity and stability when subjected to so many short cycles with a simple oxidative regeneration that requires no addition of halogen.

The first cycle begins upon contact of the catalyst with the hydrocarbon-containing feed, followed by contact with at least the oxidant to produce the regenerated catalyst or at least the oxidant and the optional reducing gas to produce the regenerated and reduced catalyst, and the first cycle ends upon contact of the regenerated catalyst or the regenerated and reduced catalyst with the additional quantity of the hydrocarbon-containing feed. The second and each subsequent cycle begins upon contact of the regenerated catalyst or the regenerated and reduced catalyst and the additional quantity of the hydrocarbon-containing feed and the second and each subsequent cycle ends upon contact of additional or subsequently regenerated catalyst or regenerated and reduced catalyst with the additional quantity of the hydrocarbon-containing feed.

Furthermore, unprecedented propylene yields have been obtained via the processes and catalysts described herein. In some embodiments, when the hydrocarbon-containing feed includes propane and the upgraded hydrocarbon includes propylene, contacting the hydrocarbon-containing feed with the catalyst can produce a propylene yield of at least 52%, at least 53%, at least 55%, at least 57%, at least 60%, at least 62%, or at least 63% at a propylene selectivity of at least 75%, at least 80%, at least 85%, at least 90%, or at least 95% for at least 15, at least 20, at least 30, at least 40, at least 50, at least 60, at least 70, at least 100 cycles, at least 125 cycles, at least 150 cycles, at least 175 cycles, or at least 200 cycles. In other embodiments, when a hydrocarbon-containing feed includes at least 70 vol % of propane, based on a total volume of the hydrocarbon-containing feed, is contacted under a propane partial pressure of at least 20 kPa-absolute, a propylene yield of at least 52%, at least 53%, at least 55%, at least 57%, at least 60%, at least 62%, or at least 63% at a propylene selectivity of at least 75%, at least 80%, at least 85%, at least 90%, or at least 95% can be obtained for at least 15, at least 20, at least 30, at least 40, at least 50, at least 60, at least 70, at least 100 cycles, at least 125 cycles, at least 150 cycles, at least 175 cycles, or at least 200 cycles. It is believed that the propylene yield can be further increased to at least 65%, at least 67%, at least 68%, at least 70%, at least 72%, at least 75%, at least 77%, at least 80%, or at least 82% at a propylene selectivity of at least 75%, at least 80%, at least 85%, at least 90%, or at least 95% for at least 15 cycles, at least 20, at least 30, at least 40, at least 50, at least 60, at least 70, at least 100 cycles, at least 125 cycles, at least 150 cycles, at least 175 cycles, or at least 200 cycles by further optimizing the composition of the support and/or adjusting one or more process conditions. In some embodiments, the propylene yield can be obtained when the catalyst is contacted with the hydrocarbon feed at a temperature of at least 620° C., at least 630° C., at least 640° C., at least 650° C., at least 655° C., at least 660° C., at least 670° C., at least 680° C., at least 690° C., at least 700° C., or at least 750° C. for at least 15, at least 20, at least 30, at least 40, at least 50, at least 60, at least 70, at least 100 cycles, at least 125 cycles, at least 150 cycles, at least 175 cycles, or at least 200 cycles. Such a high propylene yield under such processing conditions was not thought possible.

Hydrocarbon Upgrading Process

The hydrocarbon-containing feed and the catalyst can be contacted with one another within any suitable environment such as one or more reaction or conversion zones disposed within one or more reactors to produce the effluent and the coked catalyst. In some embodiments, the reaction or conversion zone can be disposed or otherwise located within one or more fixed bed reactors, one or more fluidized or moving bed reactors, one or more reverse flow reactors, or any combination thereof.

The hydrocarbon-containing feed and catalyst can be contacted at a temperature in a range from 300° C., 350° C., 400° C., 450° C., 500° C., 550° C., 600° C., 620° C., 650° C., 660° C., 670° C., 680° C., 690° C., or 700° C. to 725° C., 750° C., 760° C., 780° C., 800° C., 825° C., 850° C., 875° C., or 900° C. In some embodiments, the hydrocarbon-containing feed and catalyst can be contacted at a temperature of at least 620° C., at least 650° C., at least 660° C., at least 670° C., at least 680° C., at least 690° C., or at least 700° C. to 725° C., 750° C., 760° C., 780° C., 800° C., 825° C., 850° C., 875° C., or 900° C. The hydrocarbon-containing feed can be introduced into the reaction or conversion zone and contacted with the catalyst therein for a time period of ≤3 hours, ≤2.5 hours, ≤2 hours, ≤1.5 hours, ≤1 hour, ≤45 minutes, ≤30 minutes, ≤20 minutes, ≤10 minutes, ≤5 minutes, ≤1 minute, ≤30 seconds, ≤10 seconds, ≤5 seconds, or ≤1 second or ≤0.5 second. In some embodiments, the hydrocarbon-containing feed can be contacted with the catalyst for a time period in a range from 0.1 seconds, 0.5 seconds, 0.7 seconds, 1 second, 30 second, 1 minute, 5 minutes, or 10 minutes to 30 minutes, 50 minutes, 70 minutes, 1.5 hours, 2 hours, or 3 hours.

The hydrocarbon-containing feed and catalyst can be contacted under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatics in the hydrocarbon-containing feed. In some embodiments, the hydrocarbon partial pressure during contact of the hydrocarbon-containing feed and the catalyst can be in a range from 20 kPa-absolute, 50 kPa-absolute, 100 kPa-absolute, at least 150 kPa, at least 200 kPa 300 kPa-absolute, 500 kPa-absolute, 750 kPa-absolute, or 1,000 kPa-absolute to 1,500 kPa-absolute, 2,500 kPa-absolute, 4,000 kPa-absolute, 5,000 kPa-absolute, 7,000 kPa-absolute, 8,500 kPa-absolute, or 10,000 kPa-absolute, where the hydrocarbon partial pressure is the total partial pressure of any $C_2$-$C_{16}$ alkanes and any $C_8$-$C_{16}$ alkyl aromatics in the hydrocarbon-containing feed. In other embodiments, the hydrocarbon partial pressure during contact of the hydrocarbon-containing feed and the catalyst can be in a range from 20 kPa-absolute, 50 kPa-absolute, 100 kPa-absolute, 150 kPa-absolute, 200 kPa-absolute, 250 kPa-absolute, or 300 kPa-absolute to 500 kPa-absolute, 600 kPa-absolute, 700 kPa-absolute, 800 kPa-absolute, 900 kPa-absolute, or 1,000 kPa-absolute, where the hydrocarbon partial pressure is the total partial pressure of any $C_2$-$C_{16}$ alkanes and any $C_8$-$C_{16}$ alkyl aromatics in the hydrocarbon-containing feed.

In some embodiments, the hydrocarbon-containing feed can include at least 60 vol %, at least 65 vol %, at least 70 vol %, at least 75 vol %, at least 80 vol %, at least 85 vol %, at least 90 vol %, at least 95 vol %, or at least 99 vol % of a single $C_2$-$C_{16}$ alkane, e.g., propane, based on a total volume of the hydrocarbon-containing feed. The hydrocarbon-containing feed and catalyst can be contacted under a single $C_2$-$C_{16}$ alkane, e.g., propane, pressure of at least 20 kPa-absolute, at least 50 kPa-absolute, at least 100 kPa-absolute, at least 150 kPa-absolute, at least 250 kPa-absolute, at least 300 kPa-absolute, at least 400 kPa-absolute, at least 500 kPa-absolute, or at least 1,000 kPa-absolute.

The hydrocarbon-containing feed can be contacted with the catalyst within the reaction or conversion zone at any weight hourly space velocity (WHSV) effective for carrying out the upgrading process. In some embodiments, the WHSV can be 0.01 $hr^{-1}$, 0.1 $hr^{-1}$, 1 $hr^{-1}$, 2 $hr^{-1}$, 5 $hr^{-1}$, 10 $hr^{-1}$, 20 $hr^{-1}$, 30 $hr^{-1}$, or 50 $hr^{-1}$ to 100 $hr^{-1}$, 250 $hr^{-1}$, 500 $hr^{-1}$, or 1,000 $hr^{-1}$. In some embodiments, when the hydrocarbon upgrading process includes a fluidized or otherwise moving catalyst, a ratio of the catalyst to a combined amount of any $C_2$-$C_{16}$ alkanes and any $C_8$-$C_{16}$ alkyl aromatics can be in a range from 1, 3, 5, 10, 15, 20, 25, 30, or 40 to 50, 60, 70, 80, 90, 100, 110, 125, or 150 on a weight to weight basis.

When the activity of the coked catalyst decreases below a desired minimum amount, the coked catalyst or at least a portion thereof can be contacted with the oxidant within the reaction or conversion zone or within a combustion zone that is separate and apart from the reaction or conversion zone, depending on the particular reactor configuration, to produce a regenerated catalyst. For example, regeneration of the catalyst can occur within the reaction or conversion zone when a fixed bed or reverse flow reactor is used, or within a separate combustion zone that can be separate and apart from the reaction or conversion zone when a fluidized bed reactor or other circulating or fluidized type reactor is used. Similarly, the optional reduction step can also occur within the reaction or conversion zone, within the combustion zone, and/or within a separate reduction zone. Accordingly, the hydrocarbon containing feed can be contacted with the catalyst to effect one or more of dehydrogenation, dehydroaromatization, and dehydrocyclization of at least a portion of the hydrocarbon-containing feed to produce a coked catalyst and a first effluent that includes the one or more upgraded hydrocarbons and molecular hydrogen in a cyclic type process such as those commonly employed in fixed bed and reverse flow reactors and/or a continuous type process commonly employed in fluidized bed reactors. The separation of the effluent that includes the upgraded hydrocarbon and molecular hydrogen from the coked catalyst, if needed, can be accomplished via one or more separators such as a cyclone separator.

The oxidant can be or can include, but is not limited to, $O_2$, $O_3$, $CO_2$, $H_2O$, or a mixture thereof. In some embodiments, an amount of oxidant in excess of that needed to combust 100% of the coke on the catalyst can be used to increase the rate of coke removal from the catalyst, so that the time needed for coke removal can be reduced and lead to an increased yield in the upgraded product produced within a given period of time.

The coked catalyst and oxidant can be contacted with one another at a temperature in a range from 300° C., 350° C., 400° C., 450° C., 500° C., 550° C., 600° C., 650° C., 700° C., 750° C., or 800° C. to 900° C., 950° C., 1,000° C., 1,050° C., or 1,100° C. to produce the regenerated catalyst. In some embodiments, the coked catalyst and oxidant can be contacted with one another at a temperature in a range from 500° C. to 1,100° C., 600° C. to 1,000° C., 650° C. to 950° C., 700° C. to 900° C., or 750° C. to 850° C. to produce the regenerated catalyst.

The coked catalyst and oxidant can be contacted with one another for a time period of ≤2 hours, ≤1 hour, ≤30 minutes, ≤10 minutes, ≤5 minutes, ≤1 min, ≤30 seconds, ≤10 seconds, ≤5 seconds, or ≤1 second. For example, the coked catalyst and oxidant can be contacted with one another for a time period in a range from 2 seconds to 2 hours. In some embodiments, the coked catalyst and oxidant can be contacted for a time period sufficient to remove ≥50 wt %, ≥75 wt %, or ≥90 wt % or ≥99% of any coke disposed on the catalyst.

In some embodiments, the time period the coked catalyst and oxidant contact one another can be less than the time period the catalyst contacts the hydrocarbon-containing feed to produce the effluent and the coked catalyst. For example, the time period the coked catalyst and oxidant contact one another can be at least 90%, at least 60%, at least 30%, or at least 10% less than the time period the catalyst contacts the hydrocarbon-containing feed to produce the effluent. In other embodiments, the time period the coked catalyst and oxidant contact one another can be greater than the time period the catalyst contacts the hydrocarbon-containing feed to produce the effluent and the coked catalyst. For example, the coked catalyst and oxidant contact one another can be at least 50%, at least 100%, at least 300%, at least 500%, at least 1,000%, at least 10,000%, at least 30,000%, at least 50,000%, at least 75,000%, at least 100,000%, at least 250,000%, at least 500,000%, at least 750,000%, at least 1,000,000%, at least 1,250,000%, at least 1,500,000%, or at least 1,800,000% greater than the time period the catalyst contacts the hydrocarbon-containing feed to produce the effluent.

The coked catalyst and oxidant can be contacted with one another under an oxidant partial pressure in a range from 20 kPa-absolute, 50 kPa-absolute, 100 kPa-absolute, 300 kPa-absolute, 500 kPa-absolute, 750 kPa-absolute, or 1,000 kPa-absolute to 1,500 kPa-absolute, 2,500 kPa-absolute, 4,000 kPa-absolute, 5,000 kPa-absolute, 7,000 kPa-absolute, 8,500 kPa-absolute, or 10,000 kPa-absolute. In other embodiments, the oxidant partial pressure during contact with the coked catalyst can be in a range from 20 kPa-absolute, 50 kPa-absolute, 100 kPa-absolute, 150 kPa-absolute, 200 kPa-absolute, 250 kPa-absolute, or 300 kPa-absolute to 500 kPa-absolute, 600 kPa-absolute, 700 kPa-absolute, 800 kPa-absolute, 900 kPa-absolute, or 1,000 kPa-absolute to produce the regenerated catalyst.

Without wishing to be bound by theory, it is believed that at least a portion of the Group 8-10 element, e.g., Pt, disposed on the coked catalyst can be agglomerated as compared to the catalyst prior to contact with the hydrocarbon-containing feed. It is believed that during combustion of at least a portion of the coke on the coked catalyst that at least a portion of the Group 8-10 element can be re-dispersed about the support. Re-dispersing at least a portion of any agglomerated Group 8-10 element can increase the activity and improve the stability of the catalyst over many cycles.

In some embodiments, at least a portion of the Group 8-10 element, e.g., Pt, in the regenerated catalyst can be at a higher oxidized state as compared to the Group 8-10 element in the catalyst contacted with the hydrocarbon-containing feed and as compared to the Group 8-10 element in the coked catalyst. As such, as noted above, in some embodiments the process can optionally include contacting at least a portion of the regenerated catalyst with a reducing gas to produce a regenerated and reduced catalyst. Suitable reducing gases (reducing agent) can be or can include, but are not limited to, $H_2$, CO, $CH_4$, $C_2H_6$, $C_3H_8$, $C_2H_4$, $C_3H_6$, steam, or a mixture thereof. In some embodiments, the reducing agent can be mixed with an inert gas such as Ar, Ne, He, $N_2$, $CO_2$, $H_2O$ or a mixture thereof. In such embodiments, at least a portion of the Group 8-10 element in the regenerated and reduced catalyst can be reduced to a lower oxidation state, e.g., the elemental state, as compared to the Group 8-10 element in the regenerated catalyst. In this embodiment, the additional quantity of the hydrocarbon-containing feed can be contacted with at least a portion of the regenerated catalyst and/or at least a portion of the regenerated and reduced catalyst.

In some embodiments, the regenerated catalyst and the reducing gas can be contacted at a temperature in a range from 300° C., 350° C., 400° C., 450° C., 500° C., 550° C., 600° C., 620° C., 650° C., or 670° C. to 720° C., 750° C., 800° C., or 900° C. The regenerated catalyst and the reducing gas can be contacted for a time period in a range from 1 second, 5 seconds, 10 seconds, 20 seconds, 30 seconds, or 1 minute to 10 minutes, 30 minutes, or 60 minutes. The regenerated catalyst and reducing gas can be contacted at a reducing agent partial pressure of 20 kPa-absolute, 50 kPa-absolute, or 100 kPa-absolute, 300 kPa-absolute, 500 kPa-absolute, 750 kPa-absolute, or 1,000 kPa-absolute to 1,500 kPa-absolute, 2,500 kPa-absolute, 4,000 kPa-absolute, 5,000 kPa-absolute, 7,000 kPa-absolute, 8,500 kPa-absolute, or 10,000 kPa-absolute. In other embodiments, the reducing agent partial pressure during contact with the regenerated catalyst can be in a range from 20 kPa-absolute, 50 kPa-absolute, 100 kPa-absolute, 150 kPa-absolute, 200 kPa-absolute, 250 kPa-absolute, or 300 kPa-absolute to 500 kPa-absolute, 600 kPa-absolute, 700 kPa-absolute, 800 kPa-absolute, 900 kPa-absolute, or 1,000 kPa-absolute to produce the regenerated catalyst.

At least a portion of the regenerated catalyst, the regenerated and reduced catalyst, new or fresh catalyst, or a mixture thereof can be contacted with an additional quantity of the hydrocarbon-containing feed within the reaction or conversion zone to produce additional effluent and additional coked catalyst. As noted above, the cycle time from the contacting the hydrocarbon-containing feed with the catalyst to the contacting the additional quantity of the hydrocarbon-containing feed with at least a portion of the regenerated catalyst, and/or the regenerated and reduced catalyst, and optionally with new or fresh catalyst can be ≤5 hours.

In some embodiments, one or more additional feeds, e.g., one or more sweep fluids, can be utilized between flows of the hydrocarbon-containing feed and the oxidant, between the oxidant and the optional reducing gas if used, between the oxidant and the additional hydrocarbon-containing feed, and/or between the reducing gas and the additional hydrocarbon-containing feed. The sweep fluid can, among other things, purge or otherwise urge undesired material from the reactors, such as non-combustible particulates including soot. In some embodiments, the additional feed(s) can be inert under the dehydrogenation, dehydroaromatization, and dehydrocyclization, combustion, and/or reducing conditions. Suitable sweep fluids can be of can include, $N_2$, He, Ar, $CO_2$, $H_2O$, $CO_2$, $CH_4$, or a mixture thereof. In some embodiments, if the process utilizes a sweep fluid the duration or time period the sweep fluid is used can be in a range from 1 second, 5 seconds, 10 seconds, 20 seconds, 30 seconds, or 1 minute to 10 minutes, 30 minutes, or 60 minutes.

As noted above, the first cycle begins upon contact of the catalyst with the hydrocarbon-containing feed, followed by contact with at least the oxidant to produce the regenerated catalyst or at least the oxidant and the optional reducing gas to produce the regenerated and reduced catalyst, and the first cycle ends upon contact of the regenerated catalyst or the regenerated and reduced catalyst with the additional quantity of the hydrocarbon-containing feed. If any sweep fluid is utilized between flows of the hydrocarbon-containing feed and the oxidant, between the oxidant and the reducing gas (if used), between the oxidant and the additional quantity of the hydro-carbon containing feed, and/or between the reducing gas (if used) and the additional quantity of the hydrocarbon-containing feed is used, the period of time such sweep fluid is utilized would be included in the period included in the cycle time. As such, the cycle time from the contacting the hydrocarbon-containing feed with the catalyst in step (I) to the contacting the additional quantity of the hydrocarbon-containing feed with the regenerated catalyst in step (III) can be ≤5 hours.

Systems suitable for carrying out the processes disclosed herein can include systems that are well-known in the art such as the fixed bed reactors disclosed in WO Publication No. WO2017078894; the fluidized riser reactors and/or downer reactors disclosed in U.S. Pat. Nos. 3,888,762; 7,102,050; 7,195,741; 7,122,160; and 8,653,317; and U.S. Patent Application Publication Nos. 2004/0082824; 2008/0194891; and the reverse flow reactors disclosed in U.S. Pat. No. 8,754,276; U.S. Patent Application Publication No. 2015/0065767; and WO Publication No. WO2013169461.

Catalyst

The catalyst can include 0.05 wt %, 0.1 wt %, 0.2 wt %, 0.5 wt %, or 1 wt % to 2 wt %, 3 wt %, 4 wt %, 5 wt %, or 6 wt % of the Group 8-10 element, based on the total weight of the support. In some embodiments, the catalyst can include >0.025 wt %, >0.05 wt %, >0.1 wt %, 0.13 wt %, 0.15 wt %, 0.17 wt %, 0.2 wt %, 0.2 wt %, 0.23, 0.25 wt %, 0.27 wt %, or >0.3 wt % and <0.5 wt %, <1 wt %, <2 wt %, <3 wt %, <4 wt %, <5 wt %, or <6 wt % of the Group 8-10 element based on the total weight of the support. In some embodiments, the Group 8-10 element can be or can include, but is not limited to, Fe, Co, Ni, Ru, Pd, Os, Ir, Pt, a combination thereof, or a mixture thereof. In at least one embodiment, the Group 8-10 element can be or can include Pt.

The support can be or can include, but is not limited to, one or more elements having an atomic number of 4, 12, 20-22, 30, 38-40, 48, or 56-71. Said another way, the support can be or can include one or more Group 2 elements, one or more Group 4 elements, one or more Group 12 elements, one or more elements having an atomic number of 21, 39, or 57-71, combinations thereof, or mixture thereof. In some embodiments, the Group 2 element, the Group 4 element, the Group 12 element, and/or the element having an atomic number of 21, 39, or 57-71 can be present in its elemental form. In other embodiments, the Group 2 element, the Group 4 element, the Group 12 element, and/or the element having an atomic number of 21, 39, or 57-71 can be present in the form of a compound. For example, the Group 2 element, the Group 4 element, the Group 12 element, and/or the element having an atomic number of 21, 39, or 57-71 can be present as an oxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, or a silicide. In some embodiments, a mixture of any two or more compounds that include the Group 2 element, the Group 4 element, the Group 12 element, and/or the element having an atomic number of 21, 39, or 57-71 can be present in different forms. For example, a first compound can be an oxide and a second compound can be an aluminate where the first compound and the second compound include the same or different Group 2 element, Group 4 element, Group 12 element, and/or element having an atomic number of 21, 39, or 57-71, with respect to one another.

In some embodiments, the support can be or can include at least one of: w wt % of the one or more Group 2 elements, x wt % of the one or more Group 4 elements, y wt % of the one or more Group 12 elements, and z wt % of the one or more elements having an atomic number of 21, 39, or 57-71 based on the weight of the support, where w, x, y, and z are independently in a range from 0 to 100. Any Group 2 element present in the support can be associated with a wt % m based on the weight of the support, any Group 4 element present in the support can be associated with a wt % n based on the weight of the support, any Group 12 element present in the support can be associated with a wt % p based on the weight of the support, and any element having an atomic number of 21, 39, or 57-71 present in the support can be associated with a wt % q based on the weight of the support, where m, n, p, and q can independently be a number that is in a range from 1 to 100. In some embodiments, a sum of w/m+x/n+y/p+z/q can be at least 1, based on the weight of the support. In other embodiments, a sum of w/m+x/n+y/p+z/q can be at least 1, at least 2, at least 4, at least 6, at least 8, at least 12, at least 24, at least 48, or at least 60, based on the weight of the support. In other embodiments, a sum of w/m+x/n+y/p+z/q can be in a range from 1, 2, 3, 4, 5, 6, 7, or 8 to 10, 12, 16, 24, 30, 48, or 60. In other embodiments, a sum of w/m+x/n+y/p+z/q can be in a range from 1 to 2, 2 to 4, 4 to 6, 6 to 8, 8 to 12, 12 to 24, 24 to 48, or 48 to 60.

In some embodiments, m can be one of ten values selected from: 2, 4, 6, 8, 10, 12, 14, 16, 18, and 20; n can be one of twelve values selected from: 2, 4, 6, 8, 10, 12, 14, 16, 18, 20, 22, and 24; p can be one of twelve values selected from: 2, 4, 6, 8, 10, 12, 14, 16, 18, 20, 22, and 24; and q can be one of twelve values selected from: 2, 4, 6, 10, 14, 18, 22, 26, 30, 34, 38, and 40, where m, n, p, and q can be any combination such that there are 17,280 (10×12×12×12) distinct combinations. In other embodiments, m can be equal to 2, 7, 10, or 20, n can be 2, 10, 20, or 25, p can be 2, 10, 20, or 25, and q can be 2, 10, 30, or 40, where m, n, p, and q can be any combination such that there are 256 (4×4×4×4) distinct combinations. In some embodiments, m, n, p, and q can each be equal to 2, 10, 15, or 30. In other embodiments, m can be equal to 7, n can be equal to 10, p can be equal to 10, and q can be equal to 10. In other embodiments, m can be equal to 7, n can be equal to 20, p can be equal to 20, and q can be equal to 10. In other embodiments, m can be equal to 10, n can be equal to 20, p can be equal to 20, and q can be equal to 30. In other embodiments, m can be equal to 7, n can be equal to 10, p can be equal to 10, and q can be equal to 30.

In some embodiments, w, x, y, and z can independently be 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100, where a sum of w, x, y, z is ≤100.

In some embodiments, when the support includes the Group 2 element, a molar ratio of the Group 2 element to the Group 8-10 element can be in a range from 0.24, 0.5, 1, 10, 50, 100, 300, 450, 600, 800, 1,000, 1,200, 1,500, 1,700, or 2,000 to 3,000, 3,500, 4,000, 4,500, 5,000, 5,500, 6,000, 6,500, 7,000, 7,500, 8,000, 8,500, 9,000, or 9,500. In some embodiments, when the support includes the Group 4 element, a molar ratio of the Group 4 element to the Group 8-10 element can be in a range from 0.18, 0.3, 0.5, 1, 10, 50, 100, or 200 to 300, 400, 500, 600, 700, or 810. In some embodiments, when the support includes the Group 12 element, a molar ratio of the Group 12 element to the Group 8-10 element can be in a range from 0.29, 0.5, 1, 10, 50, or 100 to 200, 300, 400, 500, or 590. In some embodiments, when the support includes the element having an atomic number of 21, 39, or 57-71, a molar ratio of the element having an atomic number of 21, 39, or 57-71 to the Group 8-10 element can be in a range from 0.19, 0.5, 1, 10, 50, 100, or 150 to 200, 250, 300, 350, 400, or 438. In some embodiments, when the support includes two or more of the Group 2, 4, or 12 element and the element having an atomic number of 21, 39, or 57-71, a molar ratio of a combined amount of any Group 2 element, any Group 4 element, any Group 12 element, and any element having an atomic number of 21, 39, or 57-71 to the Group 8-10 element can be in a range from 0.18, 0.5, 1, 10, 50, 100, 300, 450, 600, 800, 1,000, 1,200, 1,500, 1,700, or 2,000 to 3,000, 3,500, 4,000, 4,500, 5,000, 5,500, 6,000, 6,500, 7,000, 7,500, 8,000, 8,500, 9,000, or 9,500.

In some embodiments, the support can be or can include, but is not limited to, one or more of the following compounds: $Mg_uZn_{1-u}O$, where u is a positive number; $Zn_vAl2O3_{+v}$, where v is a positive number; $Mg_wAl_2O_{3+w}$, where w is a positive number; $Ca_xAl_2O_{3+x}$, where x is a positive number; $Sr_yAl_2O_{3+y}$, where y is a positive number; $Ba_zAl_2O_{3+z}$, where z is a positive number. BeO; MgO; CaO; BaO; SrO; $BeCO_3$; $MgCO_3$; $CaCO_3$; $SrCO_3$, $BaCO_3$; $ZrO_2$; ZrC; ZrN; $ZrSiO_4$; $CaZrO_3$; $Ca_7ZrA_{16}O_{18}$; $TiO_2$; TiC; TiN; $TiSiO_4$; $CaTiO_3$; $Ca_7Al_6O_{18}$; $HfO_2$; HfC; HfN; $HfSiO_4$; $HfZrO_3$; $Ca_7HfAl_6O_{18}$; ZnO; $Zn_3(PO_4)_2$; $Zn(ClO_3)_2$; $ZnSO_4$; $B_2O_6Zn_3$; $Zn_3N_2$; $ZnCO_3$; $CeO_2$; $Y_2O_3$; $La_2O_3$; $Sc_2O_3$; $Pr_6O_{11}$; $CePO_4$; $CeZrO_4$; $CeAlO_3$; $BaCeO_3$; $CePO_4$; Yttria-stabilized $ZrO_2$; one or more magnesium chromates, one or more magnesium tungstates, one or more magnesium molybdates combinations thereof, and mixtures thereof.

The $Mg_uZn_{1-u}O$, where u is a positive number, if present as the support or as a component of the support can have a molar ratio of Mg to Zn in a range from 1, 2, 3, or 6 to 12, 25, 50, or 100. The $Zn_vAl2O_{3+v}$, where v is a positive number, if present as the support or as a component of the support can have a molar ratio of Zn to Al in a range from 0.05, 0.3, or 0.6 to 0.9, 1.5, or 3 The $Mg_wAl_2O_{3+w}$, where w is a positive number, if present as the support or as a component of the support can have a molar ratio of Mg to Al in a range from 1, 2, 3, 4, or 5 to 6, 7, 8, 9, or 10. The $Ca_xAl_2O_{3+x}$, where x is a positive number, if present as the support or as a component of the support can have a molar ratio of Ca to Al in a range from 1:12, 1:4, 1:2, 2:3, 5:6, 1:1, 12:14, or 1.5:1. In some embodiments, the $Ca_xAl_2O_3$, can include tricalcium aluminate, dodecacalcium hepta-aluminate, moncalcium aluminate, moncalcium dialuminate, monocalcium hexa-aluminate, dicalcium aluminate, pentacalcium trialuminate, tetracalcium trialuminate, or any mixture thereof. The $Sr_yAl_2O_{3+y}$, where y is a positive number, if present as the support or as a component of the support can have a molar ratio of Sr to Al in a range from 0.05, 0.3, or 0.6 to 0.9, 1.5, or 3. The $Ba_zAl_2O_{3+z}$, where z is a positive number, if present as the support or as a component of the support can have a molar ratio of Ba to Al 0.05, 0.3, or 0.6 to 0.9, 1.5, or 3.

In some embodiments, the support can also include, but is not limited to, at least one metal element and/or at least one metalloid element selected from Groups 5, 6, 7, 11, 13, 14, 15, and 16 and/or at least one compound thereof. If the support also includes a compound that includes the metal element and/or metalloid element selected from Groups 5, 6, 7, 11, 13, 14, 15, and 16, the compound can be present in the support as an oxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, or a silicide. In some embodiments, suitable compounds that include the metal element and/or metalloid element selected from Groups 5, 6, 7, 11, 13, 14, 15, and 16 can be or can include, but are not limited to, one or more of the following: $B_2O_3$, $AlBO_3$, $Al_2O_3$, $SiO_2$, $SiC$, $Si_3N_4$, an aluminosilicate, $VO$, $V_2O_3$, $VO_2$, $V_2O_5$, $Ga_2O_3$, $In_2O_3$, $Mn_2O_3$, $Mn_3O_4$, $MnO$, one or more molybdenum oxides, one or more tungsten oxides, one or more zeolites, and mixtures and combinations thereof.

In some embodiments, the support can also include one or more promoters disposed thereon. The promoter can be or can include, but is not limited to, Sn, Ga, Zn, Ge, In, Re, Ag, Au, Cu, a combination thereof, or a mixture thereof. As such, the Zn, Ga, and/or In, if present as a component of the catalyst, can be present as a component of the support, as a promoter disposed on the support, or both as a component of the support and as a promoter disposed on the support. In some embodiments, the promoter can be associated with the Group 8-10 element, e.g., Pt. For example, the promoter and the Group 8-10 element disposed on the support can form Group-8-10 element-promoter clusters that can be dispersed on the support. The promoter, if present, can improve the selectivity/activity/longevity of the catalyst for a given upgraded hydrocarbon. In some embodiments, the addition of the promoter can improve the propylene selectivity of the catalyst when the hydrocarbon-containing feed includes propane. The catalyst can include the promoter in an amount of 0.01 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 3 wt %, 5 wt %, 7 wt %, or 10 wt %, based on the weight of the support.

In some embodiments, the support can also include one or more alkali metal elements disposed on the support. The alkali metal element, if present, can be or can include, but is not limited to, Li, Na, K, Rb, Cs, a combination thereof, or a mixture thereof. In at least some embodiments, the alkali metal element ca be or can include K and/or Cs. The alkali metal element, if present, can improve the selectivity of the catalyst for a given upgraded hydrocarbon. The catalyst can include the alkali metal element in an amount 0.01 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 2 wt %, 3 wt %, 4 wt %, or 5 wt %, based on the weight of the support.

The preparation of the support can be accomplished via any known process. For simplicity and ease of description, the preparation of a suitable support that includes a mixed oxide of magnesium and aluminum (Mg(Al)O or MgO/$Al_2O_3$) support will be described in more detail. Catalyst synthesis techniques are well-known and the following description is for illustrative purposes and not to be considered as limiting the synthesis of the support or the catalyst. In some embodiments, to make the MgO/$Al_2O_3$ mixed oxide support, Mg and Al precursors such as $Mg(NO_3)_2$ and $Al(NO_3)_3$ can be mixed together, e.g., ball-milled, followed by calcination. In another embodiment, the two precursors can be dissolved in $H_2O$, stirred until dry (with heat optionally applied), followed by calcination. In another embodiment, the two precursors can be dissolved in $H_2O$, followed by the addition of a base and a carbonate, e.g., NaOH/$Na_2CO_3$ to produce hydrotalcite, followed by calcination. In another embodiment, a commercial ready MgO and $Al_2O_3$ may be mixed and ball-milled. In another embodiment, the $Mg(NO_3)_2$ precursor can be dissolved in $H_2O$ and the solution can be impregnated onto an existing support, e.g., an $Al_2O_3$ support, that can be dried and calcined. In another embodiment, Mg from $Mg(NO_3)_2$ can be loaded onto an existing $Al_2O_3$ support through ion adsorption, followed by liquid-solid separation, drying and calcination.

Group 8-10 metals and any promoter and/or any alkali metal element may be loaded onto the mixed oxide support by any known technique. For example, one or more Group 8-10 element precursors, e.g., chloroplatinic acid, tetramineplatinum nitrate, and/or tetramineplatinum hydroxide, one or more promoter precursors (if used), e.g., a salt such as $SnCl_4$ and/or $AgNO_3$, and one or more alkali metal element precursors (if used), e.g., $KNO_3$, $KCl$, and/or $NaCl$, can be dissolved in water. The solution can be impregnated onto the support, followed by drying and calcination. In some embodiments, the Group 8-10 element precursor and optionally the promoter precursor and/or the alkali metal element precursor can be loaded onto the support at the same time, or separately in a sequence separated by drying and/or calcination steps. In other embodiments, the Group 8-10 element and, optionally the promoter and/or alkali metal element, can be loaded onto the support by chemical vapor deposition, where the precursors are volatilized and deposited onto the support, followed by calcination. In other embodiments, the Group 8-10 element precursor and, optionally, the promoter precursor and/or alkali metal precursor, can be loaded onto the support through ion adsorption, followed by liquid-solid separation, drying and calcination. Optionally, the catalyst can also be synthesized using a one-pot synthesis method where the precursors of the support, group 8-10 metal active phase and the promoters are all mixed together, dry or wet, with or without any other additives to aid the synthesis, followed by drying and calcination.

Suitable processes that can be used to prepare the catalysts disclosed herein can include the processes described in U.S. Pat. Nos. 4,788,371; 4,962,265; 5,922,925; 8,653,317; EP Patent No. EP0098622; Journal of Catalysis 94 (1985), pp. 547-557; and/or Applied Catalysis 54 (1989), pp. 79-90.

The as-synthesized catalyst, when examined under scanning electron microscope or transmission electron microscope, can appear as either primary particles, as agglomerates of primary particles, as aggregated primary particles, or a combination thereof. The primary particles in the as-synthesized catalyst, when examined under scanning electron microscope or transmission electron microscope, can have an average particle size, e.g., a diameter when spherical, in a range from 0.2 nm, 0.5 nm, 1 nm, 5 nm, 10 nm, 25 nm, 30 nm, 40 nm 50 nm, 60 nm, 70 nm, 80 nm, 90 nm, 100 nm, 150 nm, 200 nm, 250 nm, 300 nm, 350 nm, 400 nm, 450 nm, or 500 nm to 1 μm, 10 μm, 25 μm, 50 μm, 100 μm, 150 μm, 200 μm, 250 μm, 300 μm, 400 μm, or 500 μm. In some embodiments, the catalyst the discrete particles can have an average cross-sectional length of 0.2 nm to 500 μm, 0.5 nm to 300 μm, 1 nm to 200 μm, 2 nm to 100 μm, or 2 nm to 500 nm as measured by a transmission electron microscope.

The catalyst can have a surface area in a range from 0.1 $m^2/g$, 1 $m^2/g$, 10 $m^2/g$, or 100 $m^2/g$ to 500 $m^2/g$, 800 $m^2/g$, 1,000 $m^2/g$, or 1,500 $m^2/g$. The surface area of the catalyst can be measured according to the Brunauer-Emmett-Teller (BET) method using adsorption-desorption of nitrogen (temperature of liquid nitrogen, 77 K) with a Micromeritics 3flex instrument after degassing of the powders for 4 hrs at 350° C. More information regarding the method can be found, for example, in "Characterization of Porous Solids and Powders: Surface Area, Pore Size and Density," S. Lowell et al., Springer, 2004.

In some embodiments, the support can be extruded or otherwise formed into any desired monolithic structure and the Group 8-10 element and any optional promoter and/or alkali metal element can be disposed thereon. Suitable monolithic structures can be or can include, but are not limited to, structures having a plurality of substantially parallel internal passages such as those in the form of a ceramic honeycomb. In some embodiments, the support can be in the form of beads, spheres, rings, toroidal shapes, irregular shapes, rods, cylinders, flakes, films, cubes, polygonal geometric shapes, sheets, fibers, coils, helices, meshes, sintered porous masses, granules, pellets, tablets, powders, particulates, extrudates, cloth or web form materials, honeycomb matrix monolith, including in comminuted or crushed forms, and the Group 8-10 element and any optional promoter and/or alkali metal element can be disposed thereon.

The as-synthesized catalyst can be formulated into one or more appropriate forms for different short cycle (≤5 hours) hydrocarbon upgrading processes. Alternatively, the support can be formulated into appropriate forms for different short cycle hydrocarbon upgrading processes, before the addition of the Group 8-10 element and, any optional promoter and/or alkali metal element. During formulation, one or more binders and/or additives can be added to the catalyst and/or support to improve the chemical/physical properties of the catalyst. For example, spray-dried catalyst particles having an average cross-sectional area in a range from 40 μm to 80 μm are typically used in an FCC type fluid-bed reactor. To make spray-dried catalyst, the support/catalyst needs to be made into a slurry with binder/additive in the slurry before spray-drying and calcination.

Hydrocarbon-Containing Feed

The $C_2$-$C_{16}$ alkanes can be or can include, but are not limited to, ethane, propane, n-butane, isobutane, n-pentane, isopentane, n-hexane, 2-methylpentane, 3-methylpentane, 2,2-dimethylbutane, n-heptane, 2-methylhexane, 2,2,3-trimethylbutane, cyclopentane, cyclohexane, methylcyclopentane, ethylcyclopentane, n-propylcyclopentane, 1,3-dimethylcyclohexane, or a mixture thereof. For example, the hydrocarbon-containing feed can include propane, which can be dehydrogenated to produce propylene, and/or isobutane, which can be dehydrogenated to produce isobutylene. In another example, the hydrocarbon-containing feed can include liquid petroleum gas (LP gas), which can be in the gaseous phase when contacted with the catalyst. In some embodiments, the hydrocarbon in the hydrocarbon-containing feed can be composed of substantially a single alkane such as propane. In some embodiments, the hydrocarbon-containing feed can include ≥50 mol %, ≥75 mol %, ≥95 mol %, ≥98 mol %, or ≥99 mol % of a single $C_2$-$C_{16}$ alkane, e.g., propane, based on a total weight of all hydrocarbons in the hydrocarbon-containing feed. In some embodiments, the hydrocarbon-containing feed can include at least 50 vol %, at least 55 vol %, at least 60 vol %, at least 65 vol %, at least 70 vol %, at least 75 vol %, at least 80 vol %, at least 85 vol %, at least 90 vol %, at least 95 vol %, at least 97 vol %, or at least 99 vol % of a single $C_2$-$C_{16}$ alkane, e.g., propane, based on a total volume of the hydrocarbon-containing feed.

The $C_8$-$C_{16}$ alkyl aromatics can be or can include, but are not limited to, ethylbenzene, propylbenzene, butylbenzene, one or more ethyl toluenes, or a mixture thereof. In some embodiments, the hydrocarbon-containing feed can include ≥50 mol %, ≥75 mol %, ≥95 mol %, ≥98 mol %, or ≥99 mol % of a single $C_8$-$C_{16}$ alkyl aromatic, e.g., ethylbenzene, based on a total weight of all hydrocarbons in the hydrocarbon-containing feed. In some embodiments, the ethylbenzene can be dehydrogenated to produce styrene. As such, in some embodiments, the processes disclosed herein can include propane dehydrogenation, butane dehydrogenation, isobutane dehydrogenation, pentane dehydrogenation, pentane dehydrocyclization to cyclopentadiene, naphtha reforming, ethylbenzene dehydrogenation, ethyltoluene dehydrogenation, and the like.

In some embodiments, the hydrocarbon-containing feed can be diluted, e.g., with one or more diluents such as one or more inert gases. Suitable inert gases can be or can include, but are not limited to, Ar, Ne, He, $N_2$, $CO_2$, $CH_4$, or a mixture thereof. If the hydrocarbon containing-feed includes a diluent, the hydrocarbon-containing feed can include 0.1 vol %, 0.5 vol %, 1 vol %, or 2 vol % to 3 vol %, 8 vol %, 16 vol %, or 32 vol % of the diluent, based on a total volume of any $C_2$-$C_{16}$ alkanes and any $C_8$-$C_{16}$ alkyl aromatics in the hydrocarbon-containing feed.

In some embodiments, the hydrocarbon-containing feed can also include $H_2$. In some embodiments, when the hydrocarbon-containing feed includes $H_2$, a molar ratio of the $H_2$ to a combined amount of any $C_2$-$C_{16}$ alkane and any $C_8$-$C_{16}$ alkyl aromatic can be in a range from 0.1, 0.3, 0.5, 0.7, or 1 to 2, 3, 4, 5, 6, 7, 8, 9, or 10.

In some embodiments, the hydrocarbon-containing feed can be substantially free of any steam, e.g., <0.1 vol % of steam, based on a total volume of any $C_2$-$C_{16}$ alkanes and any $C_8$-$C_{16}$ alkyl aromatics in the hydrocarbon-containing feed. In other embodiments, the hydrocarbon-containing feed can include steam. For example, the hydrocarbon-containing feed can include 0.1 vol %, 0.3 vol %, 0.5 vol %, 0.7 vol %, 1 vol %, 3 vol %, or 5 vol % to 10 vol %, 15 vol %, 20 vol %, 25 vol %, 30 vol %, 35 vol %, 40 vol %, 45 vol %, or 50 vol % of steam, based on a total volume of any $C_2$-$C_{16}$ alkanes and any $C_8$-$C_{16}$ alkyl aromatics in the hydrocarbon-containing feed. In other embodiments, the hydrocarbon-containing feed can include ≤50 vol %, ≤45 vol %, ≤40 vol %, ≤35 vol %, ≤30 vol %, ≤25 vol %, ≤20 vol %, or ≤15 vol % of steam, based on a total volume of any $C_2$-$C_{16}$ alkanes and any $C_8$-$C_{16}$ alkyl aromatics in the hydrocarbon-containing feed. In other embodiments, the hydrocarbon-containing feed can include at least 1 vol %, at least 3 vol %, at least 5 vol %, at least 10 vol %, at least 15 vol %, at least 20 vol %, at least 25 vol %, or at least 30 vol % of steam, based on a total volume of any $C_2$-$C_{16}$ alkanes and any $C_8$-$C_{16}$ alkyl aromatics in the hydrocarbon-containing feed.

In some embodiments, the hydrocarbon-containing feed can include sulfur. For example, the hydrocarbon-containing feed can include sulfur in a range from 0.5 ppm, 1 ppm, 5 ppm, 10 ppm, 20 ppm 30 ppm, 40 ppm, 50 ppm, 60 ppm, 70 ppm, or 80 ppm to 100 ppm, 150 ppm, 200 ppm, 300 ppm, 400 ppm, or 500 ppm. In other embodiments, the hydrocarbon-containing feed can include sulfur in a range from 1 ppm to 10 ppm, 10 ppm to 20 ppm, 20 ppm to 50 ppm, 50 ppm to 100 ppm, or 100 ppm to 500 ppm. The sulfur, if present in the hydrocarbon-containing feed, can be or can include, but is not limited to, $H_2S$, dimethyl disulfide, as one or more mercaptans, or any mixture thereof.

The hydrocarbon feed can be substantially free or free of molecular oxygen. In some embodiments, the hydrocarbon feed can include ≤5 mol %, ≤3 mol %, or ≤1 mol % of molecular oxygen ($O_2$). It is believed that providing a hydrocarbon feed substantially-free of molecular oxygen substantially prevents oxidative coupling reactions that would otherwise consume at least a portion of the alkane and/or the alkyl aromatic in the hydrocarbon feed.

Recovery and Use of the Upgraded Hydrocarbons

The upgraded hydrocarbon can include at least one upgraded hydrocarbon, e.g., an olefin, water, unreacted hydrocarbons, unreacted molecular hydrogen, etc. The upgraded hydrocarbon can be recovered or otherwise obtained via any convenient process, e.g., by one or more conventional processes. One such process can include cooling the effluent to condense at least a portion of any water and any heavy hydrocarbon that may be present, leaving the olefin and any unreacted alkane or alkyl aromatic primarily in the vapor phase. Olefin and unreacted alkane or alkyl aromatic hydrocarbons can then be removed from the reaction product in one or more separator drums. For example, one or more splitters can be used to separate the dehydrogenated product from the unreacted hydrocarbon feed.

In some embodiments, a recovered olefin, e.g., propylene, can be used for producing polymer, e.g., recovered propylene can be polymerized to produce polymer having segments or units derived from the recovered propylene such as polypropylene, ethylene-propylene copolymer, etc. Recovered isobutene can be used, e.g., for producing one or more of: an oxygenate such as methyl tert-butyl ether, fuel additives such as diisobutene, synthetic elastomeric polymer such as butyl rubber, etc.

EXAMPLES

The foregoing discussion can be further described with reference to the following non-limiting examples.

The following process steps were performed on the catalysts used in most examples below. All experiments were carried out at ambient pressure, except for the few exceptions as noted in the examples below.

1. A gas that included 10 vol % of $O_2$ in He, or air was passed through the catalyst at a regeneration temperature ($T_{regen}$) for a certain period of time ($T_{regen}$) to regenerate the catalyst.
2. Without changing the flow of the gas, the temperature within the reactor was changed from $T_{regen}$ to a reduction temperature ($T_{red}$).
3. The system was flushed with He gas.
4. A gas that included 10 vol % $H_2$ in Ar was passed through the catalyst at the $T_{red}$ for a certain period of time ($T_{red}$).
5. The system was flushed with He gas.
6. The temperature within the reactor from was changed from $T_{red}$ to a reaction temperature ($T_{rxn}$) in the presence of the inert gas.
7. A hydrocarbon-containing feed that included 90 vol % of $C_3H_8$ in Ar or Kr or He at a flow rate ($F_{rxn}$) was passed through the catalyst at the $T_{rxn}$ for a certain period of time ($t_{rxn}$). In some examples, the hydrocarbon-containing feed was passed through a sparger immersed in deionized water kept at a temperature of $T_1$, and then through a reflux with a carefully controlled temperature of $T_2$ before it was introduced into the reactor and reached the catalyst. When the sparger was used, the hydrocarbon feed included a certain amount of steam within the reactor, which is shown in the relevant tables below.
8. The system was flushed with He gas.
9. The gas that included 10 vol % of $O_2$ in He, or air was again passed through the catalyst at $T_{rxn}$, and the temperature within the reactor was changed from $T_{rxn}$ to $T_{regen}$.

In certain examples, the catalyst reduction step was not carried out and the following steps were performed.

1. The gas that included 10 vol % of $O_2$ in He or air was passed through the catalyst at the $T_{regen}$ for the $t_{regen}$.
2. Without changing the flow of the gas, the temperature within the reactor was changed from $T_{regen}$ to $T_{rxn}$.
3. The system was flushed with the inert gas (such as He).
4. The hydrocarbon-containing feed that included 90 vol % of $C_3H_8$ in Ar or Kr or He at a flow rate of $F_{rxn}$ was passed through the catalyst at the $T_{rxn}$ for the $t_{rxn}$. In some examples, the hydrocarbon-containing feed was passed through the sparger immersed in deionized water kept at the temperature of $T_1$, and then through a reflux with carefully controlled temperature of $T_2$ before it was introduced into the reactor and reached the catalyst.
5. The system was flushed with an inert gas (such as He).
6. The gas that included 10 vol % of $O_2$ in He or air was again passed through the catalyst at $T_{rxn}$, and the temperature within the reactor was changed from $T_{rxn}$ to $T_{regen}$.

An AGILENT® microGC 490 was used to measure the composition of the reactor effluent every 1 minute to 1.5 minutes. The concentration of each component in the reactor effluent was then used to calculate the $C_3H_6$ yield and selectivity. The $C_3H_6$ yield and the selectivity at the beginning of $t_{rxn}$ and at the end of $t_{rxn}$ is denoted as $Y_{ini}$, $Y_{end}$, $S_{ini}$, and $S_{end}$, respectively, and reported as percentages in the data tables below. For some experiments, repeated cycles were conducted to understand catalyst stability. The $C_3H_6$ yield as reported in these examples are based on carbon only.

In each example, a certain amount of the catalyst $M_{cat}$ was mixed with an appropriate amount of quartz/SiC diluent and loaded in a quartz reactor. The amount of diluent is determined so that the catalyst bed (catalyst+diluent) is largely isothermal during operation. The dead volume of the reactor was filled with quartz chips/rods.

When the reaction temperature ($T_{rxn}$) was >620° C., thermal cracking of propane/propylene became significant. Since thermal cracking of propane/propylene has a much higher selectivity to $C_1$ and $C_2$ hydrocarbons, the overall selectivity to $C_3H_6$ is reduced. The amount of thermal cracking within the reactor is related to how much quartz/SiC diluent was added into the reactor and how well the dead volume within the reactor was reduced by the packing materials. Therefore, depending on how the reactor is packed in different experiments, the performance varies. As such, the experimental results shown in different tables are not necessarily comparable to one another.

Examples 1-23, Catalyst 1

Catalyst 1: The catalyst used in Examples 1-23 (Exs. 1-23) was a Pt-based, Sn-containing catalyst supported on an Mg/Al mixed oxide support, crushed and sieved to 20-40 mesh particle size. Elemental analysis showed that the catalyst contained 0.48 wt % Pt, 1.25 wt % Sn, 67.93 wt % of Mg, and 29.23 wt % of Al, based on the total weight of the metal elements, with an Mg to Al molar ratio of about 2.58.

Table 1 shows the experimental results for Examples 1-3.

TABLE 1

|  | Ex. 1 | Ex. 2 | Ex. 3 |
|---|---|---|---|
| Catalyst | 1 | 1 | 1 |
| $M_{cat}$ (g) | 1 | 1 | 1 |
| $T_{rxn}$ (° C.) | 620 | 620 | 620 |

TABLE 1-continued

|  |  | Ex. 1 | Ex. 2 | Ex. 3 |
|---|---|---|---|---|
| $t_{rxn}$ (min) |  | 10 | 10 | 10 |
| $F_{rxn}$ (sccm) |  | 22 | 22 | 22 |
| $S_{vol}$ (%) |  | NA | NA | NA |
| $T_{red}$ (° C.) |  | 620 | NA | 620 |
| $t_{red}$ (min) |  | 1 | NA | 5 |
| $T_{regen}$ (° C.) |  | 620 | 620 | 620 |
| $t_{regen}$ (min) |  | 30 | 30 | 30 |
| Cycles |  | 35 | 1 | 1 |
| First cycle | $Y_{ini}$ | 48.1 | 21.2 | 48.2 |
|  | $Y_{end}$ | 23.2 | 6.8 | 24 |
|  | $S_{ini}$ | 98 | 96.4 | 98 |
|  | $S_{end}$ | 93.8 | 89.6 | 93.7 |

A comparison between Ex. 1 and Ex. 3 shows that the reduction of the catalyst in the presence of molecular hydrogen after the oxidative regeneration improve the propylene yield. Ex. 1 and Ex. 3 also show that the catalyst is not very sensitive to the duration of the reduction step (1 minute vs. 5 minutes) under the experimental conditions used for these examples. At other conditions, however, there might be an optimal duration for the reduction step to be carried out. FIG. 1 shows the catalyst stability results of a catalyst used in Examples 1-3 after having undergone 35 cycles (regeneration, reduction, and dehydrogenation) carried out under the same conditions used in Example 1.

Table 2 shows the experimental results for Examples 4 and 5. The results in Table 2 show that the reduction step can be carried out at different temperatures (670° C. versus 750° C.).

TABLE 2

|  |  | Ex. 4 | Ex. 5 |
|---|---|---|---|
| Catalyst |  | 1 | 1 |
| $M_{cat}$ (g) |  | 0.773 | 0.773 |
| $T_{rxn}$ (° C.) |  | 670 | 670 |
| $t_{rxn}$ (min) |  | 10 | 10 |
| $F_{rxn}$ (sccm) |  | 17 | 17 |
| $S_{vol}$ (%) |  | 11 | 11 |
| $T_{red}$ (° C.) |  | 670 | 750 |
| $t_{red}$ (min) |  | 1 | 1 |
| $T_{regen}$ (° C.) |  | 800 | 800 |
| $t_{regen}$ (min) |  | 30 | 30 |
| Cycles |  | 1 | 1 |
| First cycle | $Y_{ini}$ | 63.1 | 61.9 |
|  | $Y_{end}$ | 61.7 | 61 |
|  | $S_{ini}$ | 86.7 | 87.7 |
|  | $S_{end}$ | 87.9 | 88.3 |

Table 3 shows the experimental results for Examples 6-10. Examples 6-10 were conducted by introducing a partial plug at the exhaust of the reactor so that as the hydrocarbon-containing feed passed through the reactor at room temperature, e.g., 25° C., the pressure indicator upstream of the reactor read 1.43 bara. During the experiment, the gas volumetric flow rate in the reactor was expected to increase due to steam addition, higher T and volume expansion of the flow due to propane dehydrogenation. Therefore, the pressure within the reactor should have been significantly higher than 1.43 bara. Unfortunately, the pressure during reactor could not be monitored due to equipment limitations. Experiments 8-10 show the effect of conducting the regeneration at different temperatures and durations.

TABLE 3

|  |  | Ex. 6 | Ex. 7 | Ex. 8 | Ex. 9 | Ex. 10 |
|---|---|---|---|---|---|---|
| P (bara) |  | 1.43 | 1.43 | 1.43 | 1.43 | 1.43 |
| Catalyst |  | 1 | 1 | 1 | 1 | 1 |
| $M_{cat}$ (g) |  | 0.773 | 0.773 | 0.773 | 0.773 | 0.773 |
| $T_{rxn}$ (° C.) |  | 670 | 670 | 670 | 670 | 670 |
| $t_{rxn}$ (min) |  | 10 | 10 | 10 | 10 | 10 |
| $F_{rxn}$ (sccm) |  | 34 | 34 | 34 | 34 | 34 |
| $S_{vol}$ (%) |  | 11 | 11 | 11 | 11 | 11 |
| $T_{red}$ (° C.) |  | 670 | 660 | 680 | 670 | 670 |
| $t_{red}$ (min) |  | 1 | 1 | 1 | 1 | 1 |
| $T_{regen}$ (° C.) |  | 800 | 800 | 800 | 800 | 900 |
| $t_{regen}$ (min) |  | 30 | 30 | 30 | 45 | 30 |
| Cycles |  | 8 | 8 | 1 | 7 | 7 |
| First cycle | $Y_{ini}$ | 57.9 | 56.2 | 58.1 | 58.4 | 57.3 |
|  | $Y_{end}$ | 55.9 | 53.9 | 55.2 | 56.7 | 54.1 |
|  | $S_{ini}$ | 89 | 91 | 86.2 | 89 | 88.9 |
|  | $S_{end}$ | 89.6 | 91.7 | 87 | 89.7 | 89.5 |
| Last cycle | $Y_{ini}$ | 57.5 | 56.2 | NA | 58.5 | NA |
|  | $Y_{end}$ | 55.4 | 54.2 | NA | 57.1 | NA |
|  | $S_{ini}$ | 88.9 | 91 | NA | 88.9 | NA |
|  | $S_{end}$ | 89.7 | 91.7 | NA | 89.7 | NA |

Table 4 shows the experimental results for Examples 11-14. The result sin Table 4 shown the effect space velocity had on the performance of the catalyst.

TABLE 4

|  |  | Ex. 11 | Ex. 12 | Ex. 13 | Ex. 14 |
|---|---|---|---|---|---|
| Catalyst |  | 1 | 1 | 1 | 1 |
| $M_{cat}$ (g) |  | 0.193 | 0.193 | 0.193 | 0.193 |
| $T_{rxn}$ (° C.) |  | 670 | 670 | 670 | 700 |
| $t_{rxn}$ (min) |  | 10 | 10 | 10 | 10 |
| $F_{rxn}$ (sccm) |  | 34 | 17 | 9 | 17 |
| $S_{vol}$ (%) |  | 11 | 11 | 11 | 11 |
| $T_{red}$ (° C.) |  | 670 | 670 | 670 | 670 |
| $t_{red}$ (min) |  | 1 | 1 | 1 | 1 |
| $T_{regen}$ (° C.) |  | 800 | 800 | 800 | 800 |
| $t_{regen}$ (min) |  | 30 | 30 | 30 | 30 |
| Cycles |  | 1 | 1 | 1 | 1 |
| First cycle | $Y_{ini}$ | 54.1 | 59.3 | 60.6 | 58.5 |
|  | $Y_{end}$ | 45 | 51.9 | 56 | 44.4 |
|  | $S_{ini}$ | 95.2 | 92.8 | 89.6 | 86.3 |
|  | $S_{end}$ | 94.4 | 92.3 | 89.3 | 82.8 |

Table 5 shows the experimental results of Examples 15 and 16. Table 5 shows the effect of reduction in the presence of steam, respectively.

TABLE 5

|  |  | Ex. 15 | Ex. 16 |
|---|---|---|---|
| Catalyst |  | 1 | 1 |
| $M_{cat}$ (g) |  | 0.193 | 0.193 |
| $T_{rxn}$ (° C.) |  | 670 | 670 |
| $t_{rxn}$ (min) |  | 10 | 10 |
| $F_{rxn}$ (sccm) |  | 9 | 9 |
| $S_{vol}$ (%) |  | 11 | 11 |
| $T_{red}$ (° C.) |  | 670 | NA |
| $t_{red}$ (min) |  | 1 | NA |
| $T_{regen}$ (° C.) |  | 800 | 800 |
| $t_{regen}$ (min) |  | 30 | 30 |
| Cycles |  | 1 | 1 |
| First cycle | $Y_{ini}$ | 58.4 | 22.4 |
|  | $Y_{end}$ | 50.2 | 13.7 |
|  | $S_{ini}$ | 90.2 | 79.4 |
|  | $S_{end}$ | 89.7 | 68.7 |

Table 6 shows the results of Examples 17 and 18. Table 6 shows the effect of regeneration duration.

TABLE 6

|  |  | Ex. 17 | Ex. 18 |
|---|---|---|---|
| Catalyst |  | 1 | 1 |
| $M_{cat}$ (g) |  | 0.773 | 0.773 |
| $T_{rxn}$ (° C.) |  | 670 | 670 |
| $t_{rxn}$ (min) |  | 10 | 10 |
| $F_{rxn}$ (sccm) |  | 17 | 17 |
| $S_{vol}$ (%) |  | 11 | 11 |
| $T_{red}$ (° C.) |  | 670 | 670 |
| $t_{red}$ (min) |  | 1 | 1 |
| $T_{regen}$ (° C.) |  | 800 | 800 |
| $t_{regen}$ (min) |  | 30 | 10 |
| Cycles |  | 1 | 1 |
| First cycle | $Y_{ini}$ | 58.2 | 56.7 |
|  | $Y_{end}$ | 55.1 | 51.7 |
|  | $S_{ini}$ | 89.5 | 89.7 |
|  | $S_{end}$ | 89 | 89.1 |

Table 7 shows the results of Examples 19-22. Table 7 shows the effect the amount steam in the hydrocarbon-containing feed has on the yield and selectivity.

TABLE 7

|  |  | Ex. 19 | Ex. 20 | Ex. 21 | Ex. 22 |
|---|---|---|---|---|---|
| Catalyst |  | 1 | 1 | 1 | 1 |
| $M_{cat}$ (g) |  | 0.773 | 0.773 | 0.773 | 0.773 |
| $T_{rxn}$ (° C.) |  | 670 | 670 | 650 | 650 |
| $t_{rxn}$ (min) |  | 10 | 10 | 10 | 10 |
| $F_{rxn}$ (sccm) |  | 17 | 17 | 17 | 17 |
| $S_{vol}$ (%) |  | 3 | 11 | 11 | NA |
| $T_{red}$ (° C.) |  | 670 | 670 | 650 | 650 |
| $t_{red}$ (min) |  | 1 | 1 | 1 | 1 |
| $T_{regen}$ (° C.) |  | 670 | 670 | 650 | 650 |
| $t_{regen}$ (min) |  | 30 | 30 | 30 | 30 |
| Cycles |  | 1 | 1 | 1 | 1 |
| First cycle | $Y_{ini}$ | 54.9 | 58.5 | 56.8 | 52.1 |
|  | $Y_{end}$ | 49.9 | 55.4 | 55.3 | 22 |
|  | $S_{ini}$ | 90.7 | 90.4 | 93.6 | 90.8 |
|  | $S_{end}$ | 88.8 | 90 | 93.6 | 84.7 |

In Ex. 23, the catalyst was subjected to 49 cycles total in the presence of about 11 vol % steam. The results of Ex. 23 are shown in Table 8.

TABLE 8

|  |  | Ex. 23 |
|---|---|---|
| Catalyst |  | 1 |
| $M_{cat}$ (g) |  | 0.773 |
| $T_{rxn}$ (° C.) |  | 670 |
| $t_{rxn}$ (min) |  | 10 |
| $F_{rxn}$ (sccm) |  | 17 |
| $S_{vol}$ (%) |  | 11 |
| $T_{red}$ (° C.) |  | 670 |
| $t_{red}$ (min) |  | 1 |
| $T_{regen}$ (° C.) |  | 670 |
| $t_{regen}$ (min) |  | 30 |
| Cycles |  | 49 |
| First cycle | $Y_{ini}$ | 56.5 |
|  | $Y_{end}$ | 51.6 |
|  | $S_{ini}$ | 89.8 |
|  | $S_{end}$ | 89 |
| Last cycle | $Y_{ini}$ | 57.6 |
|  | $Y_{end}$ | 52.4 |
|  | $S_{ini}$ | 89.8 |
|  | $S_{end}$ | 88.8 |

Figure 2:
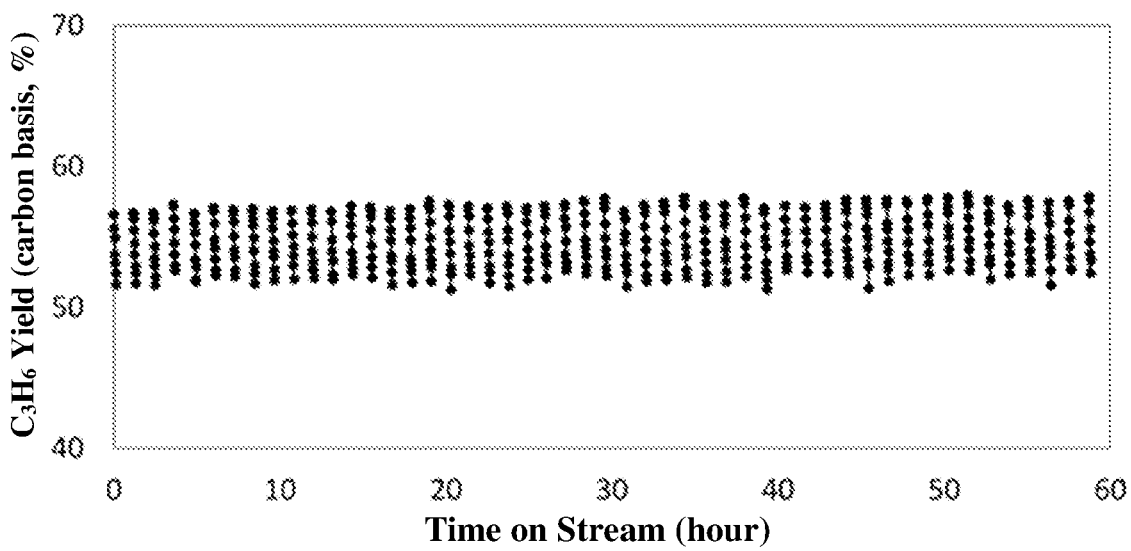
FIG. 2 shows the catalyst stability results of the catalyst used in Example 23 after having undergone 49 cycles (regeneration, reduction, and dehydrogenation) in the presence of steam.

FIG. 2 shows the catalyst stability results of the catalyst used in Example 23 after having undergone 49 cycles (regeneration, reduction, and dehydrogenation) in the presence of steam.

Example 24, Catalyst 2

The catalyst included 1 wt % of Pt and 3 wt % of Sn supported on $CeO_2$, based on the weight of the $CeO_2$. The $CeO_2$ support was made by calcining cerium (III) nitrate hexahydrate (Sigma-Aldrich 202991). The catalyst was made by incipient wetness impregnation of 3 g of $CeO_2$ with 0.788 g of 8 wt % chloroplatinic acid in water (Sigma Aldrich, 262587) and 0.266 g of tin (IV) chloride pentahydrate (Acros Organics 22369), followed by drying and calcination at 800° C. for 12 h.

TABLE 9

|  |  | Ex. 24 |
|---|---|---|
| Catalyst |  | 2 |
| $M_{cat}$ (g) |  | 0.5 |
| $T_{rxn}$ (° C.) |  | 540 |
| $t_{rxn}$ (min) |  | 10 |
| $F_{rxn}$ (sccm) |  | 12.3 |
| $S_{vol}$ (%) |  | NA |
| $T_{red}$ (° C.) |  | NA |
| $t_{red}$ (min) |  | NA |
| $T_{regen}$ (° C.) |  | 540 |
| $t_{regen}$ (min) |  | 10 |
| Cycles |  | 42 |
| First cycle | $Y_{ave}$ | 15 |
|  | $S_{ave}$ | 84.3 |
| Last cycle | $Y_{ave}$ | 14.8 |
|  | $S_{ave}$ | 89.7 |

The data in Table 9 shows that the catalyst was stable over 42 cycles.

Examples 25 and 26, Catalyst 3

The catalyst included 1 wt % of Pt and 2.7 wt % of Sn supported on Ceria-Zirconia, based on the weight of the Ceria-Zirconia. The Catalyst was made by incipient wetness impregnation of 16.5 g of Ceria-Zirconia (Sigma Aldrich 634174) with 0.44 g of chloroplatinic acid hexahydrate (BioXtra, P7082) and 1.33 g of tin (IV) chloride pentahydrate (Acros Organics 22369) dissolved in an appropriate amount of deionized water, followed by drying and calcination at 800° C. for 12 h.

TABLE 10

|  |  | Ex. 25 | Ex. 26 |
|---|---|---|---|
| Catalyst |  | 3 | 3 |
| $M_{cat}$ (g) |  | 0.456 | 0.456 |
| $T_{rxn}$ (° C.) |  | 540 | 580 |
| $t_{rxn}$ (min) |  | 10 | 10 |
| $F_{rxn}$ (sccm) |  | 11 | 11 |
| $S_{vol}$ (%) |  | NA | NA |
| $T_{red}$ (° C.) |  | NA | NA |
| $t_{red}$ (min) |  | NA | NA |
| $T_{regen}$ (° C.) |  | 540 | 580 |
| $t_{regen}$ (min) |  | 10 | 10 |
| Cycles |  | 10 | 12 |
| First cycle | $Y_{ini}$ | 22.2 | 28.6 |
|  | $Y_{end}$ | 10.6 | 9.9 |
|  | $S_{ini}$ | 85.5 | 75.9 |
|  | $S_{end}$ | 91.3 | 91 |
| Last cycle | $Y_{ini}$ | 21.4 | 28.8 |
|  | $Y_{end}$ | 11.7 | 10.4 |
|  | $S_{ini}$ | 86.2 | 76.9 |
|  | $S_{end}$ | 91.3 | 91.1 |

Examples 27-29, Catalyst 4

The catalyst included 1 wt % of Pt and 2.7 wt % of Sn supported on $Y_2O_3$, based on the weight of the $Y_2O_3$. The catalyst was made by incipient wetness impregnation of 4 g of $Y_2O_3$ (US nano 3553) with 0.106 g of chloroplatinic acid hexahydrate (BioXtra, P7082) and 0.322 g of tin (IV) chloride pentahydrate (Acros Organics 22369) dissolved in an appropriate amount of deionized water, followed by drying and calcination at 800° C. for 12 h.

TABLE 11

|  |  | Ex. 27 | Ex. 28 | Ex. 29 |
|---|---|---|---|---|
| Catalyst |  | 4 | 4 | 4 |
| $M_{cat}$ (g) |  | 0.456 | 0.456 | 0.456 |
| $T_{rxn}$ (° C.) |  | 540 | 540 | 540 |
| $t_{rxn}$ (min) |  | 10 | 10 | 10 |
| $F_{rxn}$ (sccm) |  | 11 | 11 | 11 |
| $S_{vol}$ (%) |  | NA | NA | NA |
| $T_{red}$ (° C.) |  | NA | NA | 540 |
| $t_{red}$ (min) |  | NA | NA | 30 |
| $T_{regen}$ (° C.) |  | 540 | 540 | 540 |
| $t_{regen}$ (min) |  | 10 | 20 | 10 |
| Cycles |  | 20 | 1 | 1 |
| First cycle | $Y_{ini}$ | 22.7 | 23.2 | 23.9 |
|  | $Y_{end}$ | 14.9 | 16 | 17.1 |
|  | $S_{ini}$ | 89.5 | 89.3 | 92.3 |
|  | $S_{end}$ | 94 | 94 | 94.8 |
| Last cycle | $Y_{ini}$ | 23.3 | NA | NA |
|  | $Y_{end}$ | 16.2 | NA | NA |
|  | $S_{ini}$ | 90.5 | NA | NA |
|  | $S_{end}$ | 94 | NA | NA |

The data in Table 11 shows the performance of the catalyst was stable over 20 cycles.

Examples 30-34, Catalyst 5

The catalyst included 1 wt % of Pt, 2.7 wt % of Sn supported on a $CeO_2$ and $Al_2O_3$ support. The $CeO_2$ and $Al_2O_3$ support was made by incipient wetness impregnation of 8.25 g of alumina (Sigma Aldrich 199443) with 5.67 g of cerium (III) nitrate hexahydrate (Sigma Aldrich 202991) dissolved in an appropriate amount of deionized water, followed by drying and calcination at 800° C. for 12 h. The catalyst was made by incipient wetness impregnation of the $CeO_2$ and $Al_2O_3$ support with 0.22 g of chloroplatinic acid hexahydrate (BioXtra, P7082) and 0.67 g of tin (IV) chloride pentahydrate (Acros Organics 22369) dissolved in an appropriate amount of deionized water, followed by drying and calcination at 800° C. for 12 h.

TABLE 13

|  |  | Ex. 31 | Ex. 32 | Ex. 33 | Ex. 34 |
|---|---|---|---|---|---|
| Catalyst |  | 5 | 5 | 5 | 5 |
| $M_{cat}$ (g) |  | 0.228 | 0.228 | 0.228 | 0.228 |
| $T_{rxn}$ (° C.) |  | 620 | 620 | 620 | 620 |
| $t_{rxn}$ (min) |  | 10 | 10 | 10 | 10 |
| $F_{rxn}$ (sccm) |  | 17 | 17 | 17 | 17 |
| $S_{vol}$ (%) |  | NA | 11 | NA | 11 |
| $T_{red}$ (° C.) |  | 620 | NA | NA | 620 |
| $t_{red}$ (min) |  | 1 | NA | NA | 1 |
| $T_{regen}$ (° C.) |  | 620 | 620 | 620 | 620 |
| $t_{regen}$ (min) |  | 10 | 10 | 10 | 10 |
| Cycles |  | 1 | 1 | 1 | 1 |
| First cycle | $Y_{ini}$ | 27.8 | 25.8 | 9.2 | 33.5 |
|  | $Y_{end}$ | 24.6 | 20.9 | 3.1 | 29.2 |
|  | $S_{ini}$ | 91.5 | 90.9 | 89.3 | 92 |
|  | $S_{end}$ | 92.3 | 92.3 | 81.6 | 92.7 |

The data in Table 13 shows that both the co-addition of steam and catalyst pre-reduction helped to increase the yield and selectivity.

Examples 35-38, Catalyst 6

The catalyst was 0.2 wt % of Pt, 0.2 wt % of Sn, and 0.67 wt % of K on high surface area $ZrO_2$ obtained from Alfa Aesar.

TABLE 14

|  |  | Ex. 35 | Es. 36 | Ex. 37 | Ex. 38 |
|---|---|---|---|---|---|
| Catalyst |  | 6 | 6 | 6 | 6 |
| $M_{cat}$ (g) |  | 0.57 | 0.57 | 0.57 | 0.57 |
| $T_{rxn}$ (° C.) |  | 620 | 620 | 620 | 620 |
| $t_{rxn}$ (min) |  | 10 | 10 | 10 | 10 |
| $F_{rxn}$ (sccm) |  | 10 | 10 | 10 | 10 |
| $S_{vol}$ (%) |  | 11 | NA | NA | 1 |
| $T_{red}$ (° C.) |  | 620 | NA | 620 | 620 |
| $t_{red}$ (min) |  | 1 | NA | 1 | 1 |
| $T_{regen}$ (° C.) |  | 800 | 620 | 620 | 620 |
| $t_{regen}$ (min) |  | 30 | 30 | 30 | 30 |
| Cycles |  | 24 | 1 | 1 | 1 |
| First cycle | $Y_{ini}$ | 25.7 | 7 | 8.3 | 30.6 |
|  | $Y_{end}$ | 19.4 | 6.5 | 6.8 | 25.1 |
|  | $S_{ini}$ | 78.9 | 90.4 | 90.2 | 85.7 |
|  | $S_{end}$ | 78.4 | 90.6 | 90.2 | 84.2 |
| Last cycle | $Y_{ini}$ | 24.7 | NA | NA | NA |
|  | $Y_{end}$ | 19.5 | NA | NA | NA |
|  | $S_{ini}$ | 80.7 | NA | NA | NA |
|  | $S_{end}$ | 80.2 | NA | NA | NA |

The data in Table 14 shows that the catalyst was stable over 24 cycles and that the addition of steam significantly enhanced the yield.

This disclosure can further include the following embodiments/aspects:

E1. A process for upgrading a hydrocarbon, comprising: (I) contacting a hydrocarbon-containing feed with a catalyst comprising Pt disposed on a support to effect one or more of dehydrogenation, dehydroaromatization, and dehydrocyclization of at least a portion of the hydrocarbon-containing feed to produce a coked catalyst and an effluent comprising one or more upgraded hydrocarbons and molecular hydrogen:

the hydrocarbon-containing feed comprises one or more of $C_2$-$C_{16}$ linear or branched alkanes, or one or more of $C_4$-$C_{16}$ cyclic alkanes, or one or more $C_8$-$C_{16}$ alkyl aromatics, or a mixture thereof; wherein the hydrocarbon-containing feed and catalyst are contacted at a temperature in a range from 300° C. to 900° C., for a time period of S 3 hours, under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatics in the hydrocarbon-containing feed; the catalyst comprises from 0.05 wt % to 6 wt % of Pt based on the weight of the support; and the one or more upgraded hydrocarbons comprise at least one of a dehydrogenated hydrocarbon, a dehydroaromatized hydrocarbon, and a dehydrocyclized hydrocarbon;

(II) contacting at least a portion of the coked catalyst with an oxidant to effect combustion of at least a portion of the coke to produce a regenerated catalyst lean in coke and a combustion gas; and (III) contacting an additional quantity of the hydrocarbon-containing feed with at least a portion of the regenerated catalyst to produce a re-coked catalyst and additional effluent, wherein a cycle time from the contacting the hydrocarbon-containing feed with the catalyst in step (I) to the contacting the additional quantity of the hydrocarbon-containing feed with the regenerated catalyst in step (III) is S 5 hours.

E2. The process of E1, wherein in step (I), the hydrocarbon-containing feed and catalyst are contacted in the presence of steam at an amount from 0.1 vol % to 30 vol %, based on a total volume of any $C_2$-$C_{16}$ alkanes, any $C_4$-$C_{16}$ cyclic alkanes, and any $C_8$-$C_{16}$ alkyl aromatics in the hydrocarbon-containing feed.

E3. The process of E1 or E2, wherein in step (I), the hydrocarbon-containing feed and the catalyst are contacted in the presence of steam at an amount from 1 vol % to 15 vol %, based on a total volume of any $C_2$-$C_{16}$ alkanes, any $C_4$-$C_{16}$ cyclic alkanes, and any $C_8$-$C_{16}$ alkyl aromatics in the hydrocarbon-containing feed.

E4. The process of any of E1 to E3, wherein the coked catalyst comprises agglomerated Pt disposed on the support, and wherein at least a portion of the Pt agglomerated on the support is re-dispersed about the support during combustion of the coke in step (II).

E5. The process of any of E1 to E4, wherein the hydrocarbon-containing feed comprises propane, wherein the upgraded hydrocarbon comprises propylene, and wherein contacting the hydrocarbon-containing feed with the catalyst in step (I) has a propylene yield of at least 52%, or at least 62%, or at least 72% at a propylene selectivity of ≥75%, ≥80%, ≥85%, or ≥90%, ≥95%.

E6. The process of any of E1 to E5, wherein the hydrocarbon-containing feed comprises ≥70 vol % of propane, based on a total volume of the hydrocarbon-containing feed, wherein the hydrocarbon-containing feed and catalyst are contacted under a propane partial pressure of at least 40 kPa-absolute, and wherein contacting the hydrocarbon-containing feed with the catalyst in step (I) has a propylene yield of at least 52%, or at least 62%, or at least 72% at a propylene selectivity of ≥75%, ≥80%, ≥85%, or ≥90%, ≥95%.

E7. The process of any of E1 to E6, wherein steps (I) to (III) are repeated for at least 15 cycles, wherein the catalyst has a first yield when initially contacted with the hydrocarbon-containing feed, and wherein the catalyst has a second activity upon completion of the fifteenth cycle that is at least 98% of the first yield.

E8. The process of any of E1 to E7, wherein at least a portion of the Pt in the regenerated catalyst is at a higher oxidized state as compared to the Pt in the catalyst contacted with the hydrocarbon-containing feed; the process further comprising, after step (II) and before step (III), the following step:
(IIa) contacting at least a portion of the regenerated catalyst with a reducing gas to produce a regenerated and reduced catalyst, wherein at a least a portion of the Pt in the regenerated and reduced catalyst is reduced to a lower oxidation state as compared to the Pt in the regenerated catalyst, and wherein the additional quantity of the hydrocarbon-containing feed is contacted with at least a portion of the regenerated and reduced catalyst.

E9. The process of E8, wherein in step (IIa), the regenerated catalyst and reducing gas are contacted at a temperature in a range from 450° C. to 900° C., preferably 600° C. to 900° C., more preferably 620° C. to 800° C., more preferably 650° C. to 750° C., more preferably from 670° C. to 720° C.

E10. The process of E8 or E9, wherein in step (IIa), the regenerated catalyst and reducing gas are contacted at a reducing agent partial pressure of 20 kPa-absolute to 10,000 kPa-absolute, or 50 kPa-absolute to 5,000 kPa-absolute, or 100 kPa-absolute to 1,000 kPa-absolute.

E11. The process of any one of E8 to E10, wherein at least a portion of the Pt in the regenerated and reduced catalyst is in the elemental state.

E12. The process of any of E1 to E11, wherein the hydrocarbon-containing feed further comprises an inert gas, e.g., Ar, Ne, He, $N_2$, $CH_4$, or a mixture thereof.

E13. The process of any of E1 to E12, wherein in step (I), the hydrocarbon-containing feed and catalyst are contacted at a temperature in a range from 600° C. to 900° C., preferably from 600° C. to 800° C., more preferably from 650° C. to 750° C., more preferably from 670° C. to 720° C.

E14. The process of any of E1 to E13, wherein in step (I), the hydrocarbon-containing feed and catalyst are contacted under a hydrocarbon partial pressure in a range from 20 kPa-absolute to 10,000 kPa-absolute, or 50 kPa-absolute to 5,000 kPa-absolute, or 100 kPa-absolute to 1,000 kPa-absolute.

E15. The process of any of E1 to E14, wherein in step (II), the coked catalyst and oxidant are contacted at a temperature in a range from 600° C. to 1,100° C., preferably from 650° C. to 1,000° C., more preferably from 700° C. to 900° C., more preferably from 750° C. to 850° C.

E16. The process of any of E1 to E15, wherein in step (II), the coked catalyst and oxidant are contacted under an oxidant partial pressure of 20 kPa-absolute to 10,000 kPa-absolute, or 50 kPa-absolute to 5,000 kPa-absolute, or 100 kPa-absolute to 1,000 kPa-absolute.

E17. The process of any of E1 to E16, wherein the catalyst further comprises a promoter.

E18. The process of E17, wherein the promoter comprises one or more of the following elements: Sn, Ga, Zn, Ge, In, Re, Ag, Au, Cu, a combination thereof, or a mixture thereof.

E19. The process of E17 or 18, wherein the promoter is disposed on the support.

E20. The process of any of E17 to E19, wherein the promoter is associated with the Pt.

E21. The process of any of E17 to E20, wherein the promoter and the Pt form Pt-promoter clusters that are dispersed on the support.

E22. The process of any of E17 to E21, wherein the catalyst comprises up to 10 wt % of the promoter based on the total weight of the support.

E23. The process of any of E1 to E22, wherein the catalyst further comprises an alkali metal element disposed on the support.

E24. The process of E17, wherein the alkali metal element comprises one or more of the following: Li, Na, K, Rb, Cs, a combination thereof, or a mixture thereof.

E25. The process of E23 or 24, and wherein the catalyst comprises up to 5 wt % of the alkali metal element based on the total weight of the support.

E26. The process of any of E1 to E25, wherein the support comprises at least one of: w wt % of a Group 2 element, x wt % of a Group 4 element, y wt % of a Group 12 element, and z wt % of an element having an atomic number of 21, 39, or 57-71 based on the weight of the support, wherein w, x, y, and z are independently in a range from 0 to 100, wherein:
any Group 2 element is associated with a wt % m based on the weight of the support,
any Group 4 element is associated with a wt % n based on the weight of the support,
any group 12 element is associated with a wt % p based on the weight of the support, and any element having an atomic number of 21, 39, or 57-71 is associated with a wt % q based on the weight of the support, m, n, p, and q are independently a number that is in a range from 1 to 100, and
wherein a sum of w/m+x/n+y/p+z/p is 1, based on the weight of the support.

E27. The process of E26, wherein m, n, p, and q are each equal to 1, 15, or 30, or wherein m=1, n=15, p=15, and q=1.

E28. The process of E26 or 27, wherein a molar ratio of a combined amount of any Group 2 element, any Group 4 element, any Group 12 element, and any element having an atomic number of 21, 39, or 57-71 to the Pt is at least 0.18, 0.19, 0.24, or 0.29.

E29. The process of any of E26 to E28, wherein the support further comprises at least one compound comprising at least one metal element or metalloid element selected from Groups 5, 6, 7, 11, 13, 14, 15, and 16.

E30. The process of any one of E26 to E29, wherein at least a portion of any Group 2 element, any Group 4 element, any Group 12 element, and any element having an atomic number of 21, 39, or 57-71 present in the support is an oxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, or a silicide.

E31. The process of any one of E26 to E30, wherein the support comprises one or more of the following: $Mg_uZn_{1-u}O$, where u is a positive number; $Zn_vAl2O3_{+v}$, where v is a positive number; $Mg_wAl_2O_{3+w}$, where w is a positive number; $Ca_wAl_2O_{3+x}$, where x is a positive number; $Sr_yAl_2O_{3+y}$, where y is a positive number; $Ba_zAl_2O_{3+z}$, where z is a positive number. BeO; MgO; CaO; BaO; SrO; $BeCO_3$; $MgCO_3$; $CaCO_3$; $SrCO_3$; $BaCO_3$; $ZrO_2$; ZrC; ZrN; $ZrSiO_4$; $CaZrO_3$; $Ca_7ZrAl_6O_{18}$; $TiO_2$; TiC; TiN; $TiSiO_4$; $CaTiO_3$; $Ca_7Al_6O_{18}$; $HfO_2$; HfC; HfN; $HfSiO_4$; $HfZrO_3$; $Ca_7HfAl_6O_{18}$; ZnO; $Zn_3(PO_4)_2$; $Zn(ClO_3)_2$; $ZnSO_4$; $B_2O_6Zn_3$; $Zn_3N_2$; $ZnCO_3$; $CeO_2$; $Y_2O_3$; $La_2O_3$; $Sc_2O_3$; $Pr_6O_{11}$; $CePO_4$; $CeZrO_4$; $CeAlO_3$; $BaCeO_3$; $CePO_4$; Yttria-stabilized $ZrO_2$; combinations thereof, and mixtures thereof.

E32. The process of any of E26 to E31, wherein the support further comprises one or more of the following: $B_2O_3$, $Al_2O_3$, $SiO_2$, SiC, $Si_3N_4$, an aluminosilicate, VO, $V_2O_3$, $VO_2$, $V_2O_5$, $Ga_2O_3$, $In_2O_3$, $Mn_2O_3$, $Mn_3O_4$, MnO, one or more zeolites, and mixtures and combinations thereof.

E33. The process of any of E1 to E32, wherein the cycle time is from 1 minute to 70 minutes, e.g., from 5 minutes to 45 minutes.

E34. The process of any of E1 to E32, wherein the cycle time is from 5 minutes to 300 minutes, e.g., from 10 minutes to 50 minutes.

E35. The process of any of E1 to E32, wherein the cycle time is from 0.1 seconds to 30 minutes, e.g., from 5 seconds to 10 minute.

E36. The process of any of E1 to E35, wherein the support is in the form of a plurality of primary particles comprising the Pt disposed thereon.

E37. The process of any of E1 to E36, wherein the catalyst comprises primary particles having an average cross-sectional length of 0.2 nm to 500 µm, preferably 0.5 nm to 300 µm, more preferably 1 nm to 200 µm, more preferably 5 nm to 100 µm, and still more preferably 2 nm to 100 nm, as measured by a transmission electron microscope.

E38. The process of any of E1 to E37, wherein the catalyst is in the form of a plurality of fluidized particles when contacted with the hydrocarbon-containing feed.

E39. The process of any of E1 to E36, wherein the support is a monolithic structure comprising the Pt disposed thereon.

E40. The process of any of E1 to E39, wherein the Pt is disposed on the support such that the Pt is the active component of the catalyst that effects the one or more of dehydrogenation, dehydroaromatization, and dehydrocyclization in step (I).

E41. The process of any of E1 to E40, which is a fluid bed process, a fixed bed process, or a revers flow reactor process.

E42. The process of any of E1 to E39, wherein the catalyst is in a fixed bed when contacted with the hydrocarbon-containing feed.

E43. The process of any of E1 to E42, wherein the support has a surface area of 0.1 m$^2$/g to 1,500 m$^2$/g, preferably 1 m$^2$/g to 1,000 m$^2$/g, more preferably 10 m$^2$/g to 800 m$^2$/g, more preferably 100 m$^2$/g to 500 m$^2$/g.

E44. The process of any of E1 or E4 to E43, wherein the hydrocarbon-containing feed is contacted with catalyst in the absence of any steam or in the presence of less than 0.1 vol % of steam based on a total volume of any $C_2$-$C_{16}$ alkanes, any $C_4$-$C_{16}$ cyclic alkanes, and any $C_8$-$C_{16}$ alkyl aromatics in the hydrocarbon-containing feed.

E45. The process of any of E26 to E44, wherein the catalyst comprises the Group 3 element, and where the hydrocarbon-containing feed comprises 0.1 vol % to 50 vol % of steam, based on a total volume of any $C_2$-$C_{16}$ alkanes, any $C_4$-$C_{16}$ cyclic alkanes, and any $C_8$-$C_{16}$ alkyl aromatics in the hydrocarbon-containing feed.

E46. A process for upgrading a hydrocarbon, comprising: (I) contacting a hydrocarbon-containing feed with a catalyst comprising a Group 8-10 element disposed on a support to effect one or more of dehydrogenation, dehydroaromatization, and dehydrocyclization of at least a portion of the hydrocarbon-containing feed to produce a coked catalyst and an effluent comprising one or more upgraded hydrocarbons and molecular hydrogen, wherein:

the hydrocarbon-containing feed comprises one or more of $C_2$-$C_{16}$ linear or branched alkanes, or one or more of $C_4$-$C_{16}$ cyclic alkanes, or one or more of $C_8$-$C_{16}$ alkyl aromatics, or a mixture thereof;

the hydrocarbon-containing feed and catalyst are contacted at a temperature in a range from 300° C. to 900° C., for a time period of S 3 hours, under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatics in the hydrocarbon-containing feed;

the one or more upgraded hydrocarbons comprise a dehydrogenated hydrocarbon, a dehydroaromatized hydrocarbon, a dehydrocylized hydrocarbon, or a mixture thereof; the catalyst comprises from 0.05 wt % to 6 wt % of the Group 8-10 element based on the weight of the support, and wherein the support comprises:

at least one of: w wt % of a Group 2 element, x wt % of a Group 4 element, y wt % of a Group 12 element, and z wt % of an element having an atomic number of 21, 39, or 57-71 based on the weight of the support, wherein w, x, y, and z are independently in a range from 0 to 100, wherein:

any Group 2 element is associated with a wt % m based on the weight of the support, any Group 4 element is associated with a wt % n based on the weight of the support, any group 12 element is associated with a wt % p based on the weight of the support, and any element having an atomic number of 21, 39, or 57-71 is associated with a wt % q based on the weight of the support, m, n, p, and q are independently a number that is in a range from 1 to 100, and
wherein a sum of w/m+x/n+y/p+z/p is 1, based on the weight of the support;
(II) contacting at least a portion of the coked catalyst with an oxidant to effect combustion of at least a portion of the coke to produce a regenerated catalyst lean in coke and a combustion gas; and
(III) contacting an additional quantity of the hydrocarbon-containing feed with at least a portion of the regenerated catalyst to produce a re-coked catalyst and additional effluent, wherein a cycle time from the contacting the hydrocarbon-containing feed with the catalyst in step (I) to the contacting the additional quantity of the hydrocarbon-containing feed with the regenerated catalyst in step (III) is S 5 hours.

E47. A process for upgrading a hydrocarbon, comprising: (I) contacting a hydrocarbon-containing feed with a catalyst comprising a Group 8-10 element or a compound thereof disposed on a support to effect one or more of dehydrogenation, dehydroaromatization, and dehydrocyclization of at least a portion of the hydrocarbon-containing feed to produce a coked catalyst and an effluent comprising one or more upgraded hydrocarbons and molecular hydrogen, wherein: the hydrocarbon-containing feed comprises one or more of $C_2$-$C_{16}$ linear or branched alkanes, or one or more of $C_4$-$C_{16}$ cyclic alkanes, or one or more of $C_8$-$C_{16}$ alkyl aromatics, or a mixture thereof and 0.1 vol % to 50 vol % of steam, based on a total volume of any $C_2$-$C_{16}$ alkanes and any $C_8$-$C_{16}$ alkyl aromatics in the hydrocarbon-containing feed;
the hydrocarbon-containing feed and catalyst are contacted at a temperature in a range from 300° C. to 900° C., for a time period of S 3 hours, under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatics in the hydrocarbon-containing feed; the catalyst comprises from 0.05 wt % to 6 wt % of the Group 8-10 element or a compound thereof based on the weight of the support, and wherein the upgraded hydrocarbon comprises a dehydrogenated hydrocarbon, a dehydroaromatized hydrocarbon, a dehydrocylized hydrocarbon, or a mixture thereof;
(II) contacting at least a portion of the coked catalyst with an oxidant to effect combustion of at least a portion of the coke to produce a regenerated catalyst lean in coke and a combustion gas; and
(III) contacting an additional quantity of the hydrocarbon-containing feed with at least a portion of the regenerated catalyst to produce a re-coked catalyst and additional effluent, wherein a cycle time from the contacting the hydrocarbon-containing feed with the catalyst in step (I) to the contacting the additional quantity of the hydrocarbon-containing feed with the regenerated catalyst in step (III) is S 5 hours.

E48. The process of E47, wherein the hydrocarbon-containing feed comprises 1 vol % to 15 vol % of the steam.

E49. The process of E47 or 48, wherein the support comprises:
at least one of: w wt % of a Group 2 element, x wt % of a Group 4 element, y wt % of a Group 12 element, and z wt % of an element having an atomic number of 21, 39, or 57-71 based on the weight of the support, wherein w, x, y, and z are independently in a range from 0 to 100, wherein:
any Group 2 element is associated with a wt % m based on the weight of the support,
any Group 4 element is associated with a wt % n based on the weight of the support,
any group 12 element is associated with a wt % p based on the weight of the support, and
any element having an atomic number of 21, 39, or 57-71 is associated with a wt % q based on the weight of the support,
m, n, p, and q are independently a number that is in a range from 1 to 100, and
wherein a sum of w/m+x/n+y/p+z/p is 1, based on the weight of the support E50). The process of E46 or E49, wherein m, n, p, and q are each equal to 1, or 15, or 30, or wherein m=1, n=15, p=15, and q=1.

E51. The process of any of E46 to E50, wherein the hydrocarbon-containing feed comprises propane, wherein the upgraded hydrocarbon comprises propylene, and wherein contacting the hydrocarbon-containing feed with the catalyst in step (I) has a propylene yield of at least 52%, or at least 62%, or at least 72% at a propylene selectivity of ≥75%, ≥80%, ≥85%, or ≥90%, or ≥95% at a propylene selectivity of ≥75%, ≥80%, ≥85%, or ≥90%, or 95%.

E52. The process of any of E46 to 51, wherein the hydrocarbon-containing feed comprises ≥51 vol % of propane, based on a total volume of the hydrocarbon-containing feed, wherein the hydrocarbon-containing feed and catalyst are contacted under a propane partial pressure of at least 20 kPa-absolute, and wherein contacting the hydrocarbon-containing feed with the catalyst in step (I) has a propylene yield of ≥52%, or ≥62%, or ≥72% at a propylene selectivity of ≥75%, ≥80%, ≥85%, or ≥90%, or ≥95%.

E53. The process of any of E46 to E52, wherein steps (I) to (III) are repeated for at least 15 cycles, wherein the catalyst has a first yield of the upgraded hydrocarbon when initially contacted with the hydrocarbon-containing feed, and wherein the catalyst has a second yield of the upgraded hydrocarbon upon completion of the fifteenth cycle that is ≥95%, ≥97%, ≥98%, or ≥99% of the first yield.

E54. The process of any of E46 to E53, further comprising, after step (II) and before step (III), the following step:
(IIa) contacting at least a portion of the regenerated catalyst with a reducing gas to produce a regenerated and reduced catalyst, wherein the additional quantity of the hydrocarbon-containing feed is contacted with at least a portion of the regenerated and reduced catalyst.

E55. The process of E54, wherein at least a portion of the Group 8-10 element in the regenerated catalyst is at a higher oxidized state as compared to the Group 8-10 element in the catalyst contacted with the hydrocarbon-containing feed, and wherein at a least a portion of the Group 8-10 element in the regenerated and reduced catalyst is reduced to a lower oxidation state as compared to the Group 8-10 element in the regenerated catalyst.

E56. The process of E55, wherein at least a portion of the Group 8-10 element in the regenerated and reduced catalyst is in the elemental state.

E57. The process of any one of E54 to E56, wherein in step (IIa), the regenerated catalyst and reducing gas are contacted at a temperature in a range from 450° C. to 900° C., preferably 600° C. to 900° C., more preferably 620° C. to 800° C., more preferably 650° C. to 750° C., more preferably from 670° C. to 720° C.

E58. The process of any one of E54 to E57, wherein in step (IIa), the regenerated catalyst and reducing gas are contacted at a reducing agent partial pressure of 20 kPa-absolute to 10,000 kPa-absolute, or 50 kPa-absolute to 5,000 kPa-absolute, or 100 kPa-absolute to 1,000 kPa-absolute.

E59. The process of any of E46 to E58, wherein the Group 8-10 element comprises Pt.

E60. The process of any of E46 to E59, wherein the hydrocarbon-containing feed further comprises an inert gas, e.g., Ar, Ne, He, $N_2$, $CH_4$, and mixtures thereof.

E61. The process of any of E46 to E60, wherein in step (I), the hydrocarbon-containing feed and catalyst are contacted at a temperature in a range from 650° C. to 900° C., more preferably from 650° C. to 800° C., preferably from 660° C. to 780° C., more preferably from 670° C. to 760° C.

E62. The process of any of E46 to E61, wherein in step (I), the hydrocarbon-containing feed and catalyst are contacted under a hydrocarbon partial pressure in a range from 20 kPa-absolute to 10,000 kPa-absolute, or 50 kPa-absolute to 5,000 kPa-absolute, or 100 kPa-absolute to 1,000 kPa-absolute.

E63. The process of any of E46 to E62, wherein the catalyst further comprises a promoter disposed on the support.

E64. The process of E63, wherein the promoter comprises Sn, Ga, Zn, Ge, In, Re, Ag, Au, Cu, a compound thereof, or a mixture thereof.

E65. The process of E63 or 64, wherein the promoter is associated with the Group 8-10 element.

E66. The process of any of E63 to E65, wherein the promoter and the Group 8-10 element form Group 8-10 element/promoter clusters that are dispersed on the support.

E67. The process of any of E63 to E66, wherein the catalyst comprises up to 10 wt % of the promoter based on the total weight of the support.

E68. The process of any of E46 to E67, wherein the catalyst further comprises an alkali metal disposed on the support.

E69. The process of E68, wherein the alkali metal comprises Li, Na, K, Rb, Cs, a combination thereof, or a mixture thereof.

E70. The process of E68 or 69, wherein the catalyst comprises up to 5 wt % of the alkali metal based on the total weight of the support.

E71. The process of any of E46 or E49 to E70, wherein at least a portion of any Group 2 element, any Group 4 element, any Group 12 element, and any element having an atomic number of 21, 39, or 57-71 present in the support is an oxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, or a silicide.

E72. The process of any of E46 or E49 to E71, wherein a molar ratio of a combined amount of any Group 2 element, any Group 4 element, any Group 12 element, and any element having an atomic number of 21, 39, or 57-71 to the Pt is at least 0.18.

E73. The process of any of E46 or E49 to E72, wherein the support comprises one or more of the following: $Mg_uZn_{1-u}O$, where u is a positive number; $ZnvAl2O3_{+v}$, where v is a positive number; $Mg_wAl_2O_{3+w}$, where w is a positive number; $Ca_xAl_2O_3$, where x is a positive number; $Sr_yAl_2O_{3+y}$, where y is a positive number; $Ba_zAl_2O_{3+z}$, where z is a positive number. BeO; MgO; CaO; BaO; SrO; $BeCO_3$; $MgCO_3$; $CaCO_3$; $SrCO_3$; $BaCO_3$; $ZrO_2$; ZrC; ZrN; $ZrSiO_4$; $CaZrO_3$; $Ca_7ZrAl_6O_{18}$; $TiO_2$; TiC; TiN; $TiSiO_4$; $CaTiO_3$; $Ca_7Al_6O_{18}$; $HfO_2$; HfC; HfN; $HfSiO_4$; $HfZrO_3$; $Ca_7HfAl_6O_{18}$; ZnO; $Zn_3(PO_4)_2$; $Zn(ClO_3)_2$; $ZnSO_4$; $B_2O_6Zn_3$; $Zn_3N_2$; $ZnCO_3$; $CeO_2$; $Y_2O_3$; $La_2O_3$; $SC_2O_3$; $Pr_6O_{11}$; $CePO_4$; $CeZrO_4$; $CeAlO_3$; $BaCeO_3$; $CePO_4$; Yttria-stabilized $ZrO_2$; combinations thereof, and mixtures thereof.

E74. The process of any of E46 or E49 to E73, wherein the support further comprises one or more of the following: $B_2O_3$, $Al_2O_3$, $SiO_2$, SiC, $Si_3N_4$, an aluminosilicate, VO, $V_2O_3$, $VO_2$, $V_2O_5$, $Ga_2O_3$, $In_2O_3$, $Mn_2O_3$, $Mn_3O_4$, MnO, one or more zeolites, and mixtures and combinations thereof.

E75. The process of any of E46 to E74, wherein the cycle time is from 1 minute to 70 minutes, e.g., from 5 minutes to 45 minutes.

E76. The process of any of E46 to E75, wherein the cycle time is from 5 minutes to 300 minutes, e.g., from 10 minutes to 50 minutes.

E77. The process of any of E46 to E75, wherein the cycle time is from 0.1 seconds to 30 minutes, e.g., from 5 seconds to 10 minute.

E78. The process of any of E46 to E77, wherein the support comprises a plurality of primary particles comprising the Group 8-10 element disposed thereon.

E79. The process of any of E46 to E77, wherein the catalyst comprises primary particles, and wherein the primary particles have an average cross-sectional length of 0.2 nm to 500 μm, preferably 1 nm to 300 μm, more preferably 2 nm to 200 μm, more preferably 2 nm to 100 μm, still more preferably from 2 nm to 500 nm, still more preferably from 2 nm to 100 nm, as measured by a transmission electron microscope.

E80. The process of any of E46 to E79, wherein the catalyst is in the form of a plurality of fluidized particles when contacted with the hydrocarbon-containing feed.

E81. The process of any of E46 to E77, wherein the support is a monolithic structure comprising the Group 8-10 element disposed thereon.

E82. The process of any of E46 to E81, wherein the Group 8-10 element comprises Pt, and wherein the Pt is disposed on the support such that the Pt is the active component of the catalyst that effects the one or more of dehydrogenation, dehydroaromatization, and dehydrocyclization in step (I).

E83. The process of any of E46 to E82, which is a fluid bed process, a fixed bed process, or a reverse flow reactor process.

E84. The process of any of E46 to E83, wherein the catalyst is in a fixed bed when contacted with the hydrocarbon-containing feed.

E85. The process of any of E46 to E84, wherein the support has a surface area of 0.1 $m^2/g$ to 1,500 $m^2/g$, preferably 1 $m^2/g$ to 1,000 $m^2/g$, more preferably 10 $m^2/g$ to 800 $m^2/g$, more preferably 100 $m^2/g$ to 500 $m^2/g$.

E86. The process of any of E46 or E49 to E85, wherein the catalyst comprises the Group 3 element, and where the hydrocarbon-containing feed comprises 0.1 vol % to 50 vol % of steam, based on a total volume of any $C_2$-$C_{16}$ alkanes, any $C_4$-$C_{16}$ cyclic alkanes, and any $C_8$-$C_{16}$ alkyl aromatics in the hydrocarbon-containing feed.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A process for upgrading a hydrocarbon, comprising:
(I) contacting a hydrocarbon-containing feed with a catalyst comprising Pt disposed on a support to effect one or more of dehydrogenation, dehydroaromatization, and dehydrocyclization of at least a portion of the hydrocarbon-containing feed to produce a coked catalyst and an effluent comprising one or more upgraded hydrocarbons and molecular hydrogen, wherein:
the hydrocarbon-containing feed comprises one or more of $C_2$-$C_{16}$ linear or branched alkanes, or one or more of $C_4$-$C_{16}$ cyclic alkanes, or one or more $C_5$-$C_{16}$ alkyl aromatics, or a mixture thereof;
the hydrocarbon-containing feed and catalyst are contacted at a temperature in a range from 300° C. to 900° C. under a hydrocarbon partial pressure of at least 20 kPa-absolute, wherein the hydrocarbon partial pressure is the total partial pressure of any $C_2$-$C_{16}$ alkanes and any $C_5$-$C_{16}$ alkyl aromatics in the hydrocarbon-containing feed;
the hydrocarbon-containing feed and catalyst are contacted in the presence of 0.1 vol % to 30 vol % steam, based on a total volume of the hydrocarbon-containing feed;
the catalyst comprises from >0.025 wt % to 6 wt % of Pt based on the weight of the support; and
the one or more upgraded hydrocarbons comprise at least one of a dehydrogenated hydrocarbon, a dehydroaromatized hydrocarbon, and a dehydrocyclized hydrocarbon;
(II) contacting at least a portion of the coked catalyst with an oxidant to effect combustion of at least a portion of the coke to produce a regenerated catalyst lean in coke and a combustion gas, wherein at least a portion of the Pt in the regenerated catalyst is at a higher oxidized state as compared to the Pt in the catalyst contacted with the hydrocarbon-containing feed;
(IIa) contacting at least a portion of the regenerated catalyst with a reducing gas to produce a regenerated and reduced catalyst, wherein at a least a portion of the Pt in the regenerated and reduced catalyst is reduced to a lower oxidation state as compared to the Pt in the regenerated catalyst; and
(III) contacting an additional quantity of the hydrocarbon-containing feed with at least a portion of the regenerated and reduced catalyst to produce a re-coked catalyst and additional effluent, wherein a cycle time from the contacting the hydrocarbon-containing feed with the catalyst in step (I) to the contacting the additional quantity of the hydrocarbon-containing feed with the regenerated and reduced catalyst in step (III) is ≤30 minutes.

2. The process of claim 1, wherein in step (I), the hydrocarbon-containing feed and catalyst are contacted in the presence of 0.5 vol % to 20 vol % steam, based on a total volume of the hydrocarbon-containing feed.

3. The process of claim 1, wherein the hydrocarbon-containing feed comprises propane, wherein the upgraded hydrocarbon comprises propylene, and wherein contacting the hydrocarbon-containing feed with the catalyst in step (I) has a propylene yield of at least 57% at a propylene selectivity of ≥75%.

4. The process of claim 1, wherein the hydrocarbon-containing feed comprises ≥85 vol % of propane, based on a total volume of the hydrocarbon-containing feed, wherein the hydrocarbon-containing feed and catalyst are contacted under a propane partial pressure of at least 100 kPa-absolute, and wherein contacting the hydrocarbon-containing feed with the catalyst in step (I) has a propylene yield of at least 57% at a propylene selectivity of ≥85%.

5. The process of claim 1, wherein in step (IIa), at least one of the following is met:
(i) the regenerated catalyst and reducing gas are contacted at a temperature in a range from 450° C. to 900° C.; and
(ii) the regenerated catalyst and reducing gas are contacted at a reducing agent partial pressure of 20 kPa-absolute to 10,000 kPa-absolute.

6. The process of claim 1, wherein the hydrocarbon-containing feed further comprises an inert gas.

7. The process of claim 1, wherein in step (I), at least one of the following is met:
(i) the hydrocarbon-containing feed and catalyst are contacted at a temperature in a range from 600° C. to 900° C.; and
(ii) the hydrocarbon-containing feed and catalyst are contacted under a hydrocarbon partial pressure in a range from 20 kPa-absolute to 10,000 kPa-absolute.

8. The process of claim 1, wherein in step (II), the coked catalyst and oxidant are contacted at a temperature in a range from >700° C. to 1,100° C.

9. The process of claim 1, wherein the catalyst further comprises up to 10 wt % of a promoter based on the total weight of the support, and wherein the promoter comprises one or more of the following elements: Sn, Ga, Zn, Ge, In, Re, Ag, Au, Cu, a combination thereof, or a mixture thereof.

10. The process of claim 1, wherein the catalyst further comprises up to 5 wt % of an alkali metal element based on the total weight of the support, and wherein the alkali metal element comprises one or more of the following: Li, Na, K, Rb, Cs, a combination thereof, or a mixture thereof.

11. The process of claim 1, wherein the support comprises at least 3 wt % of a Group 2 element.

12. The process of claim 1, wherein the support is produced by calcining hydrotalcite.

13. The process of claim 1, wherein in step (II), the coked catalyst and the oxidant are contacted at a temperature in a range from ≥750° C. to 1,100° C.

14. The process of claim 1, wherein in step (II), the coked catalyst and the oxidant are contacted at a temperature in a range from ≥800° C. to 1,100° C.

15. The process of claim 1, wherein in step (IIa), the regenerated catalyst and the reducing gas are contacted at a temperature in a range from >720° C. to 900° C.

16. The process of claim 1, wherein in step (IIa), the regenerated catalyst and the reducing gas are contacted at a temperature in a range from ≥750° C. to 900° C.

17. The process of claim 1, wherein in step (IIa), the regenerated catalyst and the reducing gas are contacted for a time period of <1 minute.

18. The process of claim 1, wherein in step (IIa), the regenerated catalyst and the reducing gas are contacted at a temperature >720° C. for a time period of <1 minute.

19. The process of claim 1, wherein:
in step (I), the hydrocarbon-containing feed and catalyst are contacted in the presence of 0.5 vol % to 20 vol % steam, based on a total volume of the hydrocarbon-containing feed; and
in step (IIa), the regenerated catalyst and the reducing gas are contacted at a temperature >720° C. for a time period of <1 minute.

20. A process for upgrading a hydrocarbon, comprising:
(I) contacting a hydrocarbon-containing feed with a catalyst comprising Pt disposed on a support to effect one or more of dehydrogenation, dehydroaromatization, and dehydrocyclization of at least a portion of the hydrocarbon-containing feed to produce a coked catalyst and an effluent comprising one or more upgraded hydrocarbons and molecular hydrogen, wherein:

the hydrocarbon-containing feed comprises one or more of $C_2$-$C_{16}$ linear or branched alkanes, or one or more of $C_4$-$C_{16}$ cyclic alkanes, or one or more $C_5$-$C_{16}$ alkyl aromatics, or a mixture thereof;

the hydrocarbon-containing feed and catalyst are contacted at a temperature in a range from 300° C. to 900° C. under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatics in the hydrocarbon-containing feed;

the hydrocarbon-containing feed and catalyst are contacted in the presence of 0.1 vol % to 30 vol % steam, based on a total volume of the hydrocarbon-containing feed;

the catalyst comprises from >0.025 wt % to 6 wt % of Pt based on the weight of the support;

the catalyst is in a fixed bed when contacted with the hydrocarbon-containing feed; and the one or more upgraded hydrocarbons comprise at least one of a dehydrogenated hydrocarbon, a dehydroaromatized hydrocarbon, and a dehydrocyclized hydrocarbon;

(II) contacting at least a portion of the coked catalyst with an oxidant to effect combustion of at least a portion of the coke to produce a regenerated catalyst lean in coke and a combustion gas, wherein at least a portion of the Pt in the regenerated catalyst is at a higher oxidized state as compared to the Pt in the catalyst contacted with the hydrocarbon-containing feed;

(IIa) contacting at least a portion of the regenerated catalyst with a reducing gas to produce a regenerated and reduced catalyst, wherein at a least a portion of the Pt in the regenerated and reduced catalyst is reduced to a lower oxidation state as compared to the Pt in the regenerated catalyst; and (III) contacting an additional quantity of the hydrocarbon-containing feed with at least a portion of the regenerated and reduced catalyst to produce a re-coked catalyst and additional effluent, wherein a cycle time from the contacting the hydrocarbon-containing feed with the catalyst in step (I) to the contacting the additional quantity of the hydrocarbon-containing feed with the regenerated and reduced catalyst in step (III) is ≤30 minutes.

21. The process of claim 20, wherein the support comprises at least 3 wt % of a Group 2 element.

22. A process for upgrading a hydrocarbon, comprising:
(I) contacting a hydrocarbon-containing feed with a catalyst comprising Pt disposed on a support to effect one or more of dehydrogenation, dehydroaromatization, and dehydrocyclization of at least a portion of the hydrocarbon-containing feed to produce a coked catalyst and an effluent comprising one or more upgraded hydrocarbons and molecular hydrogen, wherein:

the hydrocarbon-containing feed comprises one or more of $C_2$-$C_{16}$ linear or branched alkanes, or one or more of $C_4$-$C_{16}$ cyclic alkanes, or one or more $C_5$-$C_{16}$ alkyl aromatics, or a mixture thereof;

the hydrocarbon-containing feed and catalyst are contacted at a temperature in a range from 300° C. to 900° C. under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatics in the hydrocarbon-containing feed;

the hydrocarbon-containing feed and catalyst are contacted in the presence of 0.1 vol % to 30 vol % steam, based on a total volume of the hydrocarbon-containing feed;

the catalyst comprises from >0.025 wt % to 6 wt % of Pt based on the weight of the support;

the support comprises at least 3 wt % of a Group 2 element, the Group 2 element comprises Mg; and the one or more upgraded hydrocarbons comprise at least one of a dehydrogenated hydrocarbon, a dehydroaromatized hydrocarbon, and a dehydrocyclized hydrocarbon;

(II) contacting at least a portion of the coked catalyst with an oxidant to effect combustion of at least a portion of the coke to produce a regenerated catalyst lean in coke and a combustion gas, wherein at least a portion of the Pt in the regenerated catalyst is at a higher oxidized state as compared to the Pt in the catalyst contacted with the hydrocarbon-containing feed;

(IIa) contacting at least a portion of the regenerated catalyst with a reducing gas to produce a regenerated and reduced catalyst, wherein at a least a portion of the Pt in the regenerated and reduced catalyst is reduced to a lower oxidation state as compared to the Pt in the regenerated catalyst; and (III) contacting an additional quantity of the hydrocarbon-containing feed with at least a portion of the regenerated and reduced catalyst to produce a re-coked catalyst and additional effluent, wherein a cycle time from the contacting the hydrocarbon-containing feed with the catalyst in step (I) to the contacting the additional quantity of the hydrocarbon-containing feed with the regenerated and reduced catalyst in step (III) is ≤30 minutes.

* * * * *